US012723064B2

(12) United States Patent
Arnon et al.

(10) Patent No.: US 12,723,064 B2
(45) Date of Patent: Sep. 1, 2026

(54) TREATING ALZHEIMER'S DISEASE

(71) Applicants: Yeda Research and Development Co. Ltd., Rehovot (IL); Ramot at Tel-Aviv University Ltd., Tel-Aviv (IL)

(72) Inventors: Ruth Arnon, Rehovot (IL); Ruth Maron, Rehovot (IL); Gad Armony, Rehovot (IL); Michael Menachem Tsoory, Rehovot (IL); Meir Wilchek, Rehovot (IL); Dan Frenkel, Tel Aviv (IL)

(73) Assignees: Yeda Research and Development Co. Ltd., Rehovot (IL); Ramot at Tel-Aviv University Ltd., Tel-Aviv (IL)

( * ) Notice: Subject to any disclaimer, the term of this patent is extended or adjusted under 35 U.S.C. 154(b) by 1087 days.

(21) Appl. No.: 17/748,212

(22) Filed: May 19, 2022

(65) Prior Publication Data

US 2022/0306710 A1 Sep. 29, 2022

Related U.S. Application Data

(63) Continuation of application No. PCT/IL2020/051196, filed on Nov. 18, 2020.

(51) Int. Cl.

| | |
|---|---|
| ***C07K 14/47*** | (2006.01) |
| ***A61K 9/00*** | (2006.01) |
| ***A61P 25/28*** | (2006.01) |

(52) U.S. Cl.

CPC ........ *C07K 14/4711* (2013.01); *A61K 9/0043* (2013.01); *A61P 25/28* (2018.01)

(58) Field of Classification Search

CPC .. C07K 14/4711; C07K 2319/00; C07K 7/06; C07K 7/08; A61K 9/0043; A61K 38/1716; A61K 38/00; A61K 38/04; A61K 38/10; A61P 25/28; G01N 33/68; G01N 33/6869

See application file for complete search history.

(56) References Cited

U.S. PATENT DOCUMENTS

| | | | | |
|---|---|---|---|---|
| 2008/0050383 A1* | 2/2008 | Sigurdsson | .......... | A61K 9/0019 530/387.9 |
| 2015/0320706 A1 | 11/2015 | Imbimbo | | |
| 2018/0161395 A1* | 6/2018 | Fol | .......................... | A61P 25/28 |

FOREIGN PATENT DOCUMENTS

| | | |
|---|---|---|
| WO | WO 02/04949 | 1/2002 |
| WO | WO 2013/041962 | 3/2013 |
| WO | WO 2016/198627 | 12/2016 |
| WO | WO 2019/084488 | 5/2019 |
| WO | WO 2019/207159 | 10/2019 |
| WO | WO 2021/100041 | 5/2021 |

OTHER PUBLICATIONS

International Preliminary Report on Patentability Dated Jun. 2, 2022 From the International Bureau of WIPO Re. Application No. PCT/IL2020/051196. (8 Pages).

International Search Report and the Written Opinion Dated Feb. 11, 2021 From the International Searching Authority Re. Application No. PCT/IL2020/051196. (13 Pages).

Office Action Dated Jul. 26, 2020 From the Israel Patent Office Re. Application No. 348039. (5 Pages).

Barbato et al. "Interaction of Tau With Fe65 Links Tau to App", Neurobiology of Disease, XP004728747, 18(2): 399-408, Available Online Jan. 13, 2005.

Giaccone et al. "BetaPP and Tau Interaction. A Possible Link Between Amyloid and Neurofibrillary Tangles in Alzheimer's Disease", American Journal of Pathology, XP055770790, 148(1): 79-87, Jan. 1996.

Smith et al. "Tau Protein Directly Interacts With the Amyloid Beta-Protcin Precursor: Implications for Alzheimer's Disease", Nature Medicine, 1(4): 365-369, Apr. 1995.

Communication Pursuant to Article 94(3) EPC Dated Nov. 12, 2024 From the European Patent Office Re. Application No. 20820571.6. (5 Pages).

Communication Pursuant to Article 94(3) EPC Dated Oct. 5, 2023 From the European Patent Office Re. Application No. 20820571.6 (5 Pages).

* cited by examiner

*Primary Examiner* — Erinne R Dabkowski

(57) ABSTRACT

A method of treating Alzheimer's Disease (AD) is disclosed. The method comprises administering to the subject a therapeutically effective amount of an agent which prevents the binding of amyloid precursor protein (APP) to Tau protein.

8 Claims, 7 Drawing Sheets
(4 of 7 Drawing Sheet(s) Filed in Color)

Specification includes a Sequence Listing.

Anti Tau antibody
Anti APP antibody
70
55
180
110
APP
Tau
Protein
APP
Tau
Beads
APP+Tau
Beads
APP
Tau
Protein
APP
Tau
Beads
APP+Tau
Beads
APP
APP+Tau
Cross link

FIG. 3B

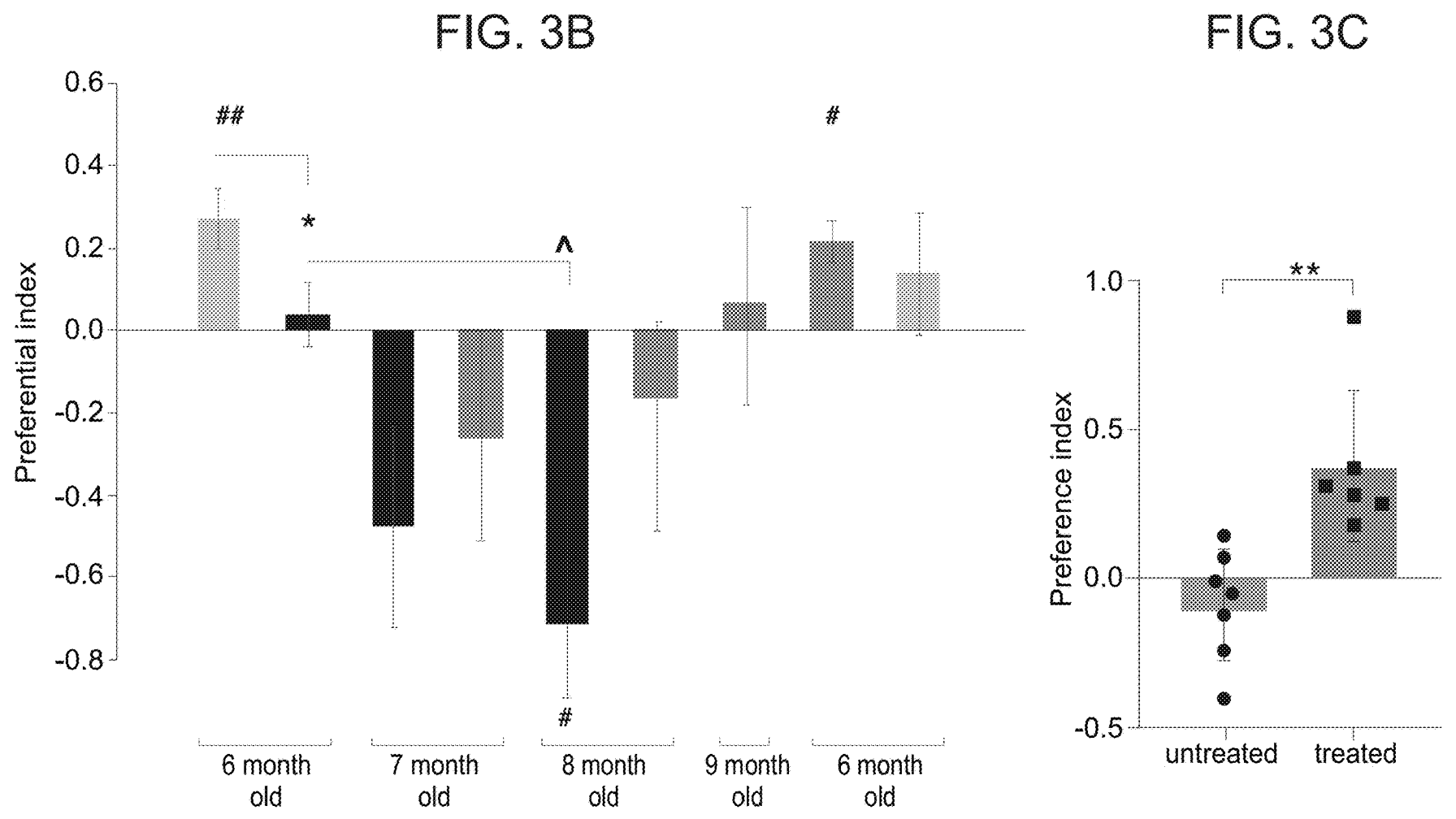

Preferential index 0.6
0.4
0.2
0.0
-0.2
-0.4
-0.6
-0.8

*
^

6 month old
7 month old
8 month old
9 month old
6 month old

FIG. 3C

Preference index 1.0
0.5
0.0
-0.5

** untreated
treated

TREATING ALZHEIMER'S DISEASE

RELATED APPLICATIONS

This application is a Continuation of PCT Patent Application No. PCT/IL2020/051196 having International filing date of Nov. 18, 2020, which claims the benefit of priority of Israeli Patent Application No. 270800 filed on Nov. 20, 2019. The contents of the above applications are all incorporated by reference as if fully set forth herein in their entirety.

SEQUENCE LISTING STATEMENT

The ASCII file, entitled 92191SequenceListing.txt, was created on May 19, 2022, and comprising 15,623 bytes. The sequence listing submitted herewith is identical to the sequence listing forming part of the international application.

FIELD AND BACKGROUND OF THE INVENTION

The present invention, in some embodiments thereof, relates to a method of treating Alzheimer's disease by preventing the association of amyloid precursor protein (APP) with Tau protein.

Alzheimer's disease (AD) is the most common form of age-associated neurodegenerative disorder clinically characterized by a decline in cognitive function or dementia. Pathologically, it is defined by the accumulation of extracellular beta-amyloid (Aß) plaques and intracellular neurofibrillary tangles (NFTs). The Aß plaques are comprised of fragments of 40 or 42 amino acid residues produced by proteolytic cleavage of the amyloid precursor protein (APP), while NFTs are composed of hyper-phosphorylated Tau protein. The causes, or mechanisms of these plaque formations and tangles are not yet well understood, but basically it is considered a protein-misfolding process that leads to the disease. The short peptide segments of the Aß plaques were demonstrated to be abnormally folded. Tau is a microtubule-associated protein expressed in the neurons that normally acts to stabilize the microtubules in the cell cytoskeleton, and is regulated by phosphorylation. Hyperphosphorylated Tau is associated with misfolding and aggregation and correlates with impaired cognitive functions. Consequently, regarding the mechanism of AD, there are two schools of thought as to whether APP (amyloid beta) or Tau are the causative factor in the disease. However, ongoing work focusing on single target therapies was disappointing and therefore, dual amyloid and Tau targeting approaches are being considered (17).

An indication for a direct interaction of Tau protein with APP was already reported (18). Furthermore, it was shown that the APP peptide spontaneously formed fibrils in vitro and in the presence of Tau, APP generated dense fibrillary assemblies containing both molecules (19). Nevertheless, no indication was provided in these studies as to the region in the Tau molecule involved in binding to APP.

SUMMARY OF THE INVENTION

According to an aspect of the present invention, there is provided a method of treating Alzheimer's Disease (AD) in a subject in need thereof comprising administering to the subject a therapeutically effective amount of an agent which prevents the binding of amyloid precursor protein (APP) to Tau protein, thereby treating the AD.

According to an aspect of the present invention, there is provided another agent which prevents the binding of amyloid precursor protein (APP) to Tau protein for use in treating AD.

According to another aspect of the present invention, there is provided a pharmaceutical composition comprising a pharmaceutically acceptable carrier and as an active agent at least one peptide which prevents the binding of amyloid precursor protein (APP) to Tau protein.

According to another aspect of the present invention, there is provided a peptide comprising at least ten consecutive amino acids of the amino acid sequence as set forth in SEQ ID NO: 1 and at least ten consecutive amino acids of the amino acid sequence as set forth in SEQ ID NO: 3, the peptide being no longer than 70 amino acids.

According to still another aspect of the present invention, there is provided a composition of matter comprising at least two peptides, wherein the first of the at least two peptides is no longer than 30 amino acids and comprises at least ten consecutive amino acids of the amino acid sequence as set forth in SEQ ID NO: 1, and the second of the at least two peptides is no longer than 30 amino acids and comprises at least ten consecutive amino acids of the amino acid sequence as set forth in SEQ ID NO: 3.

According to another aspect of the present invention, there is provided a method of identifying an agent useful for treating Alzheimer's Disease (AD) comprising analyzing the amount of a complex comprising amyloid precursor protein (APP) bound to Tau protein in the presence of the agent, wherein a downregulation in the amount of the complex in the presence of the agent compared to the amount of the complex in the absence of the agent is indicative of an agent useful for treating Alzheimer's Disease (AD).

According to some embodiments, the AD is of a type associated with a mutation in the APP or the Tau protein.

According to some embodiments, the agent comprises at least one peptide.

According to some embodiments, the binding is between lysine 370 of the APP and lysine 387 on the Tau protein.

According to some embodiments, the at least one peptide comprises at least 10 consecutive amino acids of the sequence as set forth in SEQ ID NO: 1.

According to some embodiments, the at least one peptide comprises the amino acid sequence as set forth in SEQ ID NO: 1.

According to some embodiments, the agent comprises an additional peptide which comprises at least 10 amino acids of the amino acid sequence as set forth in SEQ ID NO: 3.

According to some embodiments, the additional peptide comprises the amino acid sequence as set forth in SEQ ID NO: 3.

According to some embodiments, the at least one peptide comprises at least 10 amino acids of the amino acid sequence as set forth in SEQ ID NO: 3.

According to some embodiments, the at least one peptide comprises the amino acid sequence as set forth in SEQ ID NO: 1 and the amino acid sequence as set forth in SEQ ID NO: 3.

According to some embodiments, the amino acid sequence as set forth in SEQ ID NO: 1 is connected to the amino acid sequence as set forth in SEQ ID NO: 3 by a linker.

According to some embodiments, the at least one peptide comprises the sequence as set forth in SEQ ID NO: 5 or SEQ ID NO: 6.

According to some embodiments, the at least one peptide comprises a cell penetrating moiety.

According to some embodiments, the cell penetrating moiety comprises a cell penetrating peptide.

According to some embodiments, the e total length of the at least one peptide is no longer than 70 amino acids.

According to some embodiments, the administering comprises intranasally administering.

According to some embodiments, the at least one peptide is no longer than 70 amino acids.

According to some embodiments, the pharmaceutical composition comprises two peptides each being less than 30 amino acids, wherein the first peptide of the two peptides comprises at least 10 consecutive amino acids of the sequence as set forth in SEQ ID NO: 1 and the second peptide of the two peptides comprises at least 10 consecutive amino acids of the sequence as set forth in SEQ ID NO: 3.

According to some embodiments, the first peptide comprises the amino acid sequence as set forth in SEQ ID NO: 1.

According to some embodiments, the second peptide comprises the amino acid sequence as set forth in SEQ ID NO: 3.

According to some embodiments, the at least one peptide comprises the amino acid sequence as set forth in SEQ ID NO: 1 and the amino acid sequence as set forth in SEQ ID NO: 3.

According to some embodiments, the amino acid sequence as set forth in SEQ ID NO: 1 is connected to the amino acid sequence as set forth in SEQ ID NO: 3 by a flexible peptide linker.

According to some embodiments, the amino acid sequence as set forth in SEQ ID NO: 1 is connected to the amino acid sequence as set forth in SEQ ID NO: 3 by a rigid peptide linker.

According to some embodiments, the at least one peptide comprises the sequence as set forth in SEQ ID NO: 5.

According to some embodiments, the at least one peptide comprises the sequence as set forth in SEQ ID NO: 6.

According to some embodiments, the at least one peptide comprises a cell penetrating moiety.

According to some embodiments, the cell penetrating moiety comprises a cell penetrating peptide.

According to some embodiments, the amino acid sequence as set forth in SEQ ID NO: 1 and the amino acid sequence as set forth in SEQ ID NO: 3.

According to some embodiments, the peptide has an amino acid sequence as set forth in SEQ ID NOs: 5 or 6.

According to some embodiments, the peptide is attached to a cell penetrating moiety.

According to some embodiments, the cell penetrating moiety comprises a cell penetrating peptide.

According to some embodiments, the first of the at least two peptides comprises the amino acid sequence as set forth in SEQ ID NO: 1.

According to some embodiments, the second of the at least two peptides comprises the amino acid sequence as set forth in SEQ ID NO: 3.

According to some embodiments, the agent is a peptide or combination of peptides.

According to some embodiments, the agent is a small molecule.

According to some embodiments, the binding is between lysine 370 of the APP and lysine 387 on the Tau protein.

According to some embodiments, the complex comprises APP covalently bound to Tau protein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B, 1C:
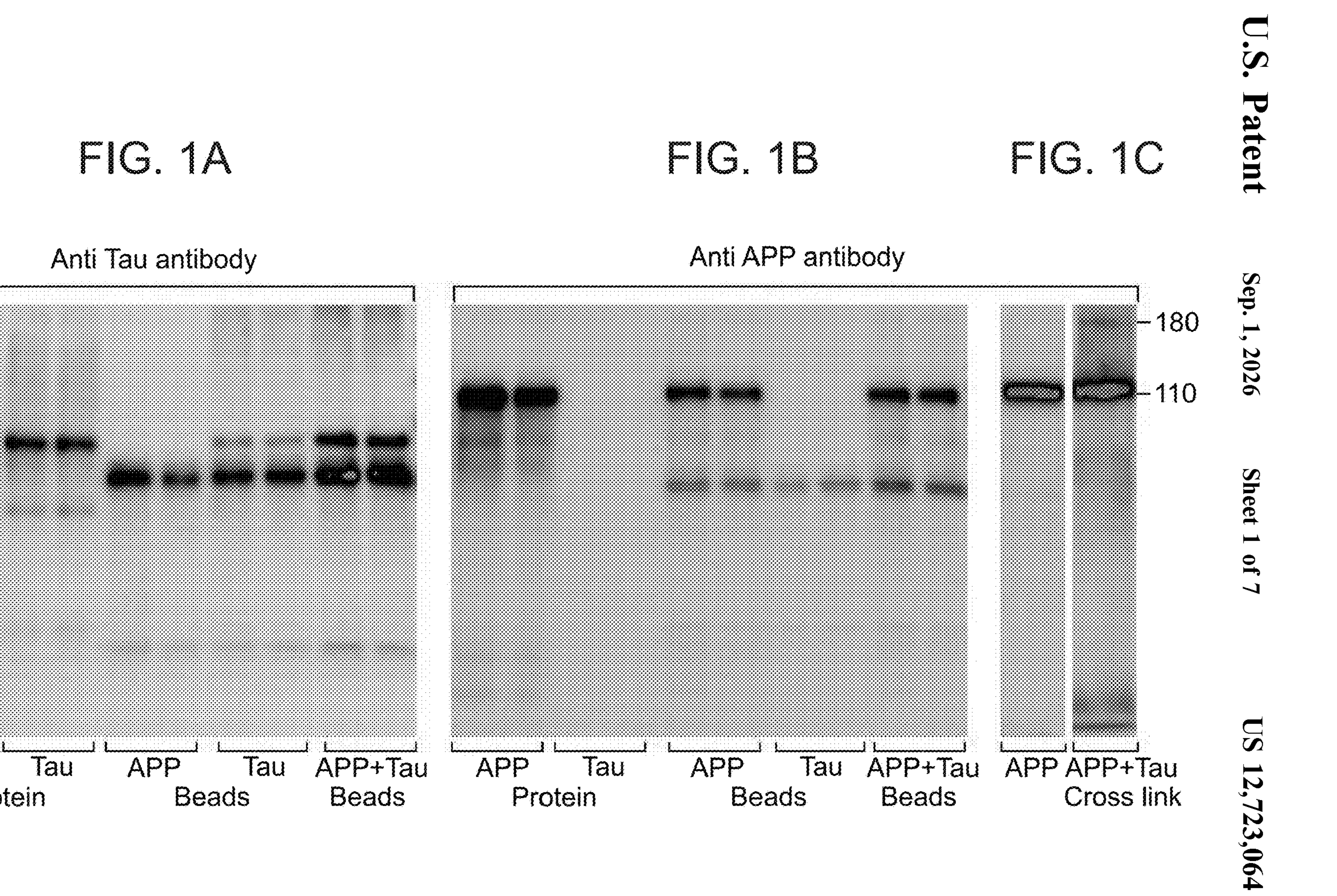

FIGS. 1A-C. Western blot of APP and Tau protein binding and crosslinking of the proteins. Samples loaded in blots A and B are 50 ng APP protein/lane and 50 ng/lane Tau protein. APP-His protein bound to protein A/G beads, previously coupled with anti-His antibodies, and Tau protein bound to protein A beads coupled with anti-His antibodies. In the last two lanes, on the right of A and B, a mixture of APP and Tau proteins was loaded. The mixture was performed by binding APP-His protein to protein A/G beads, previously coupled with anti-His antibodies, and then Tau protein was added (Materials and Methods section). Membrane A was developed with anti Tau antibody and was overexposed to enable detection of any non-specific binding of Tau (70 kD), also causing overexposure of the IgG band (55 kD). Membrane B was developed with anti Aß antibody (6E10) and shows the 110 kD band of APP protein. Membrane C was loaded with APP protein on the left lane and with a mixture of APP and Tau, crosslinked on the other lane (materials and methods section). The blot reacted with the anti Aß antibody, depicted in the left lane as APP protein (110 kD). The right lane which was loaded with the crosslinked APP and Tau proteins, shows the 110 kd band of APP as well as a 180 kD band which is the expected molecular weight of APP and Tau together. Membrane C was overexposed when developed to be able to see the 180 kD crosslinked band and therefore, the APP bands are very dark.

Figure 2A:
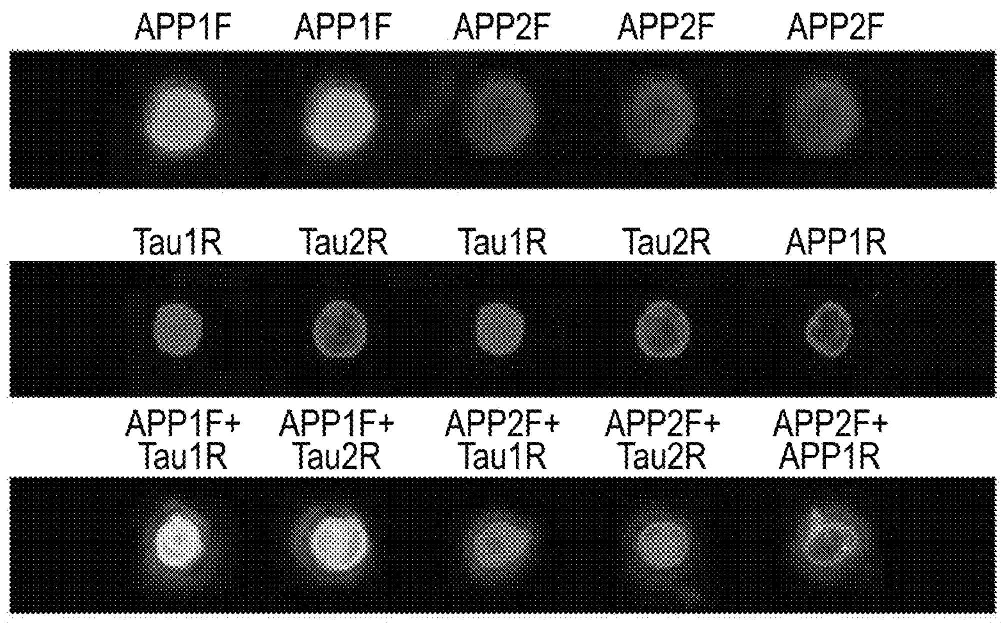
Figure 2B:
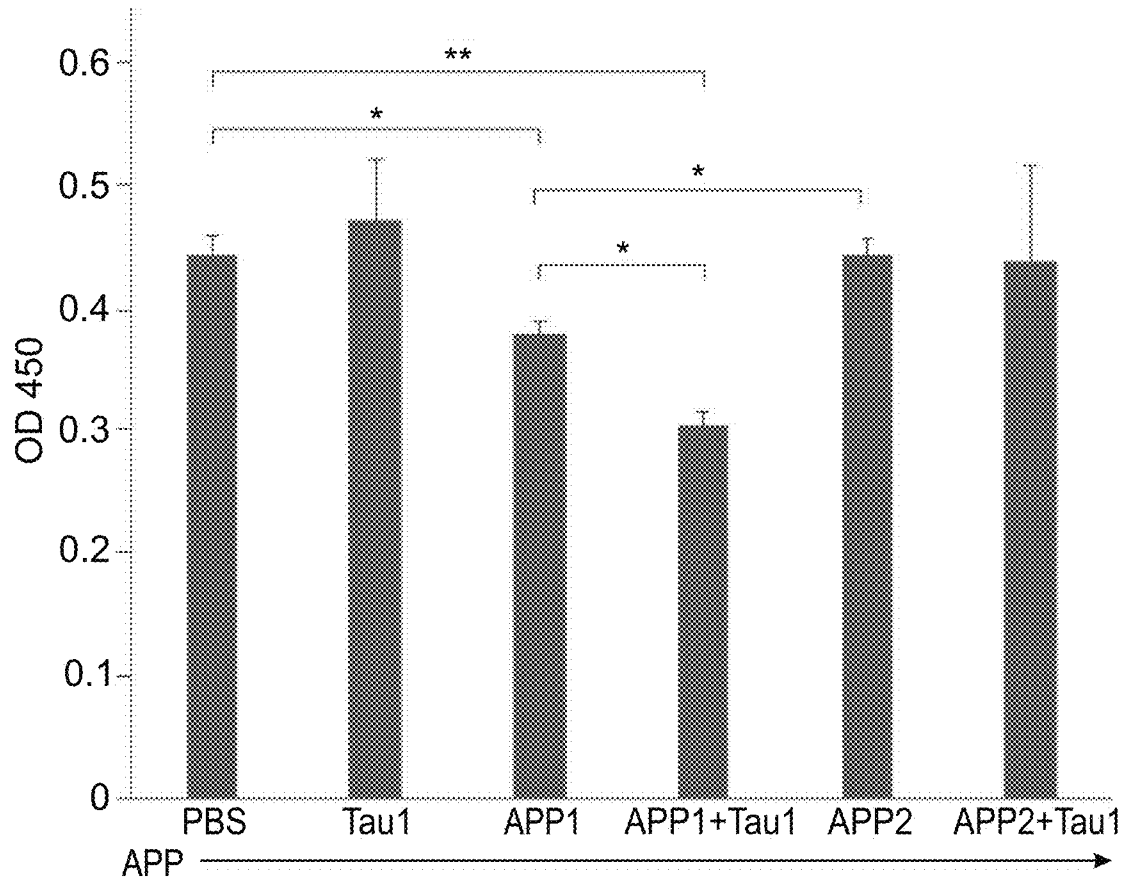

FIGS. 2A-B. Confirmation of APP and Tau peptide binding by visualization and ELISA. A) Visualization of APP and Tau peptide binding labelled by fluorescein (F) or rhodamine (R). Single labelled peptides were loaded on nitrocellulose membrane [upper row (F) and middle row (R)]. Mixtures were loaded (lower row) from left to right: APP1F+Tau1R, APP1F+Tau2R, APP2F+Tau1R and APP2F+Tau2R. Last sample was a control of APP2F+APP1R. As can be seen the only two peptides that bound to each other were APP1F and Tau1R as the color mix combination of green and red resulted in yellow (except for a faint yellow color for the combination of APP1F+Tau2R). B) Peptide inhibition of Tau and APP protein binding. An ELISA plate was coated with Tau protein overnight (ON) at 4° C. PBS, single peptides or their combinations were incubated ON at 4° C. as well. Next day, the plate was washed and blocked with PBS+3% BSA for two hours at RT. The plate was washed again with PBS. Single peptides or their combinations were added to the coated plate for four hours at RT. The plate was washed and APP protein was added to all wells for ON incubation at 4° C. The plate was then washed and anti Aß was added, to test the ability of the different peptides to affect APP protein binding to the Tau coated plate. The plate was developed with anti-mouse HRP (materials and methods section). Samples were in triplicates. Significance labelled as $p \leq 0.05$*, $p \leq 0.008$**.

Figure 3A:
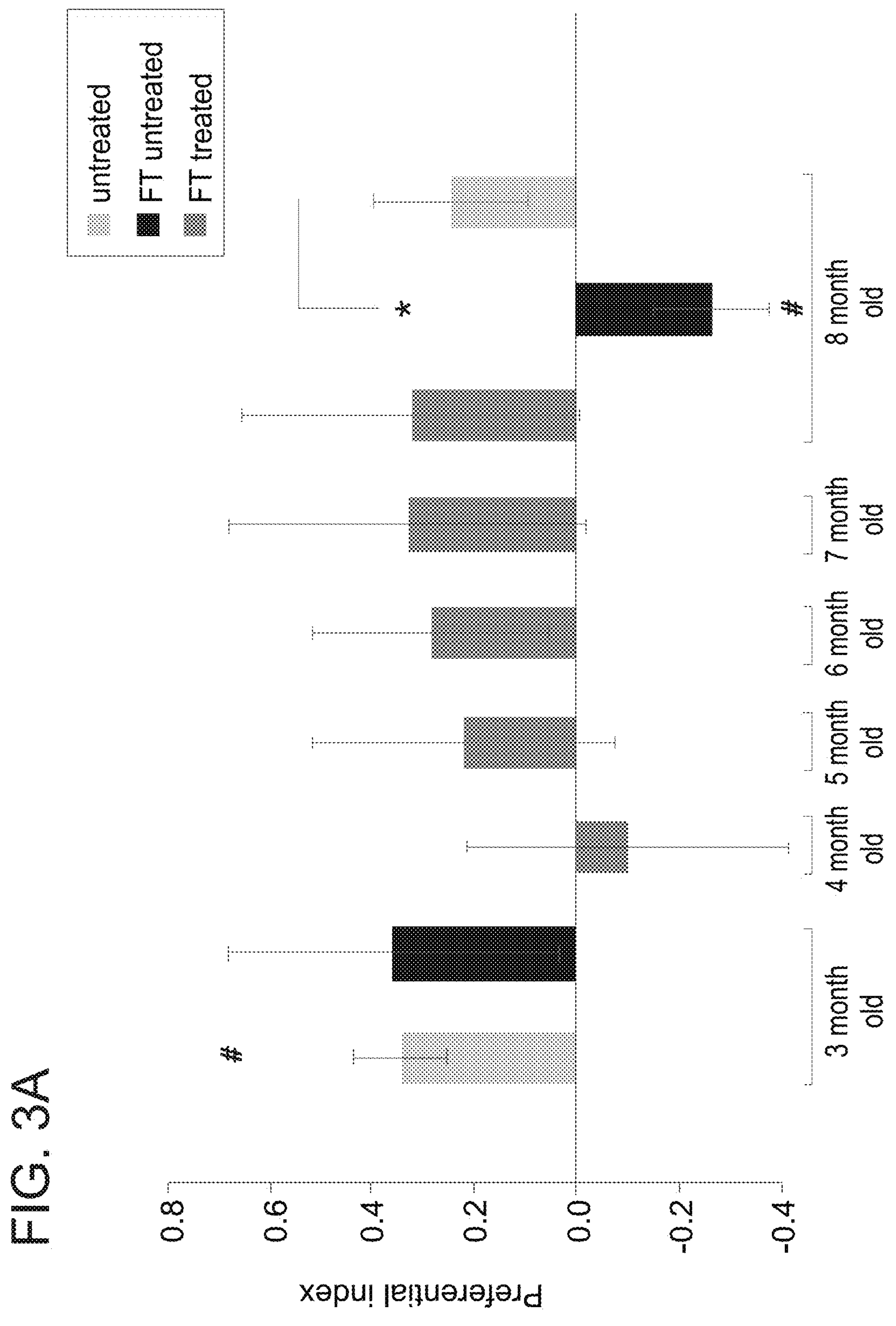

FIGS. 3A-C. In vivo, monthly behavior follow-up of 5×FAD×Tau (FT) mice treated with a mixture of APP1 and Tau1 peptides versus control PBS treated mice. A) Novel arm differential preference index among control (non-transgenic) and transgenic FT mice, treated and non-treated (PBS treated), between the age of 3 to 8 months. At the age of three months, only non-Tg control mice exhibited a significant preference to the Novel arm (#:p=0.016). The benefits of the treatment were evident at the end of the five month course. At the age of eight months, only non-treated FT mice exhibited significant poor Y-maze performance (# p=0.035) and differed significantly from non-Tg control mice (*p=0.048). Each group included 3-4 mice. B) Novelarm differential preference index among control (non-transgenic) and transgenic FT mice, treated and non-treated (PBS treated), between the age of 6 to 10 months. At the age of six months, only non-Tg control mice exhibited a significant preference for the Novel arm in the Y-maze (## p=0.002), while non-treated FT mice performed significantly worse than non-Tg controls (*: p=0.022). A significant (p=0.022) age associated cognitive decline was noted among non-treated FT between 6-8 months where eight months old non-treated FT mice performed significantly worse than six months old non-treated FT mice (^: p=0.029) and exhibited a significant negative differential preference to the Novel arm (#:p=0.028). The benefits of the treatment were evident at the end of the treatment course at the age of 10 months when only treated FT mice exhibited a significant differential preference to the Novel arm (#: p=0.024). Each group included 3-4 mice. C) Preferential index of untreated vs treated mice. FT Tg mice nasally treated with APP1+Tau1 mixture vs PBS control as described in FIG. 3B. Treatment continued between the age of 6-10 months and tested by Y-maze at the age of 10 months. Control treated mice did not recognize the Novel arm, while the APP1+Tau1 treated mice had a good cognitive score as measured by the preferential index of the Novel arm (n=6-7**p=0.0029).

FIGS. 4A-E. APP1+Tau1 mix nasally treated FT mice show reduced % plaque area, reduced brain amyloid load, in correlation with improved cognition. (A) Histological images of sagittal sections stained with anti-Aß_6E10 antibodies from brains of FT Tg mice non-treated versus nasally treated with APP1+Tau1 mixture. Treatment was given between the ages of 6 to 10 months. Histological images stained with 6E10 antibodies of 10 months old FT non-treated mice have an accumulation of a large number of Aß plaques (left panel). However, 10 months old APP1+Tau1 mixture treated mice have a significantly smaller number of plaques (right panel). Original magnification ×4. (B) Quantification of number of plaques in hippocampal sections from 5×FAD×Tau (FT) mice with or without treatment determined by 6E10 antibody staining (n=5-6 mice, * p=0.02). Original magnification ×4. C) Histological images of sections, stained with Congo red, from brains of FT Tg mice nasally treated with APP1+Tau1 mixture versus PBS control. Treatment was given between the ages of 6 to 10 months. Histological images of sections stained with Congo red of four months old FT non-treated mice already have some accumulation of Aβ plaques (left frame). However, 10 months old PBS treated mice had a much larger % area of plaques (right frame). In contrast, 10 months old APP1+Tau1 mixture treated mice had a much smaller accumulation of plaque area (middle frame). D) Quantification of % plaque area of hippocampal sections from 5×FAD×Tau (FT) mice with or without treatment determined by Congo red staining (n=6-7, *p=0.03). E) ELISA assessment of soluble Aß (1-42). The right hemisphere of each mouse in the treatment group was homogenized with PBS containing protease inhibitor and centrifuged at 40.0009 g for 40 minutes to quantify soluble Aß levels found in the supernatant. Levels of Aß (1-42) in brain samples were assessed by ELISA kit for high sensitivity human amyloid beta-42. Control PBS treated mice (n=2) versus five single mice treated with APP1+Tau1 **(p=0.006).

Figures 5A, 5B, 5C:
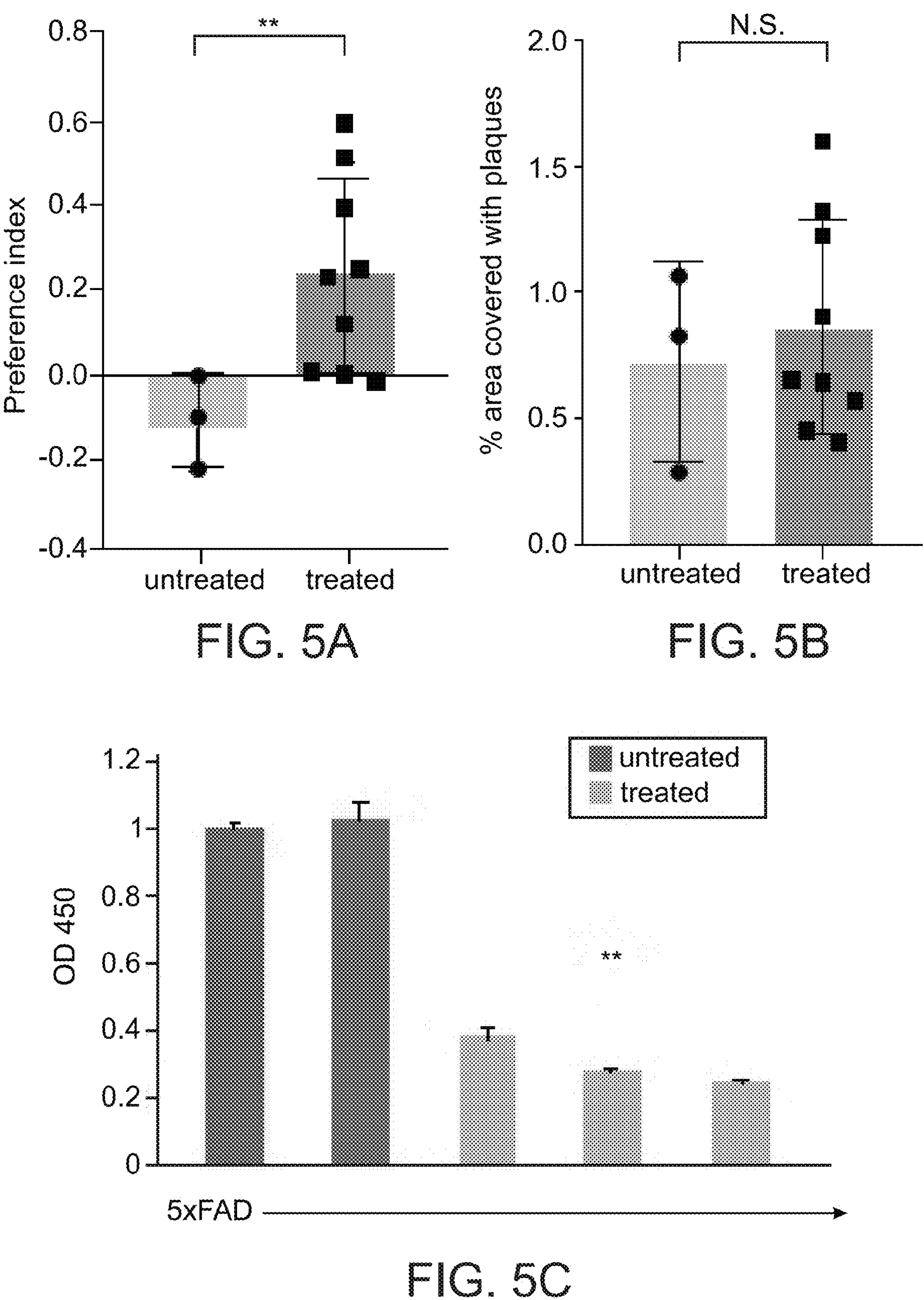

FIGS. 5A-C. FAD nasally treated mice with, APP1+Tau1, peptide mixture show improved cognition in correlation with reduced brain amyloid Aß (1-42) load.

A) Preferential index of control, PBS treated, vs mixture treated 5×FAD mice. Treatment continued between the ages of three to eight months and tested by Y maze at the age of 8 months (as described in FIG. 4A). Control PBS treated mice did not recognize the "Novel" arm, while the mixture treated mice had a good cognitive score as measured by the preferential index of the "Novel" arm. (n=3 control treated n=9 peptide treated p=0.0344).

B) Quantification of % plaque area of hippocampal sections from 5×FAD mice control treatment (PBS) vs peptide treated determined by Congo red staining (n==3 control, treated=9 p=NS).

C) ELISA assessment of soluble Aß (1-42) in brains from 5×FAD mice. Procedure was performed as described in FIG. 4E. Levels of Aß (1-42) in brain samples were assessed by ELISA kit for high sensitivity human amyloid beta-42. Control PBS treated mice (n=2) versus three single mice treated with APP1+Tau1 peptides **(p=0.0015).

Figure 6:
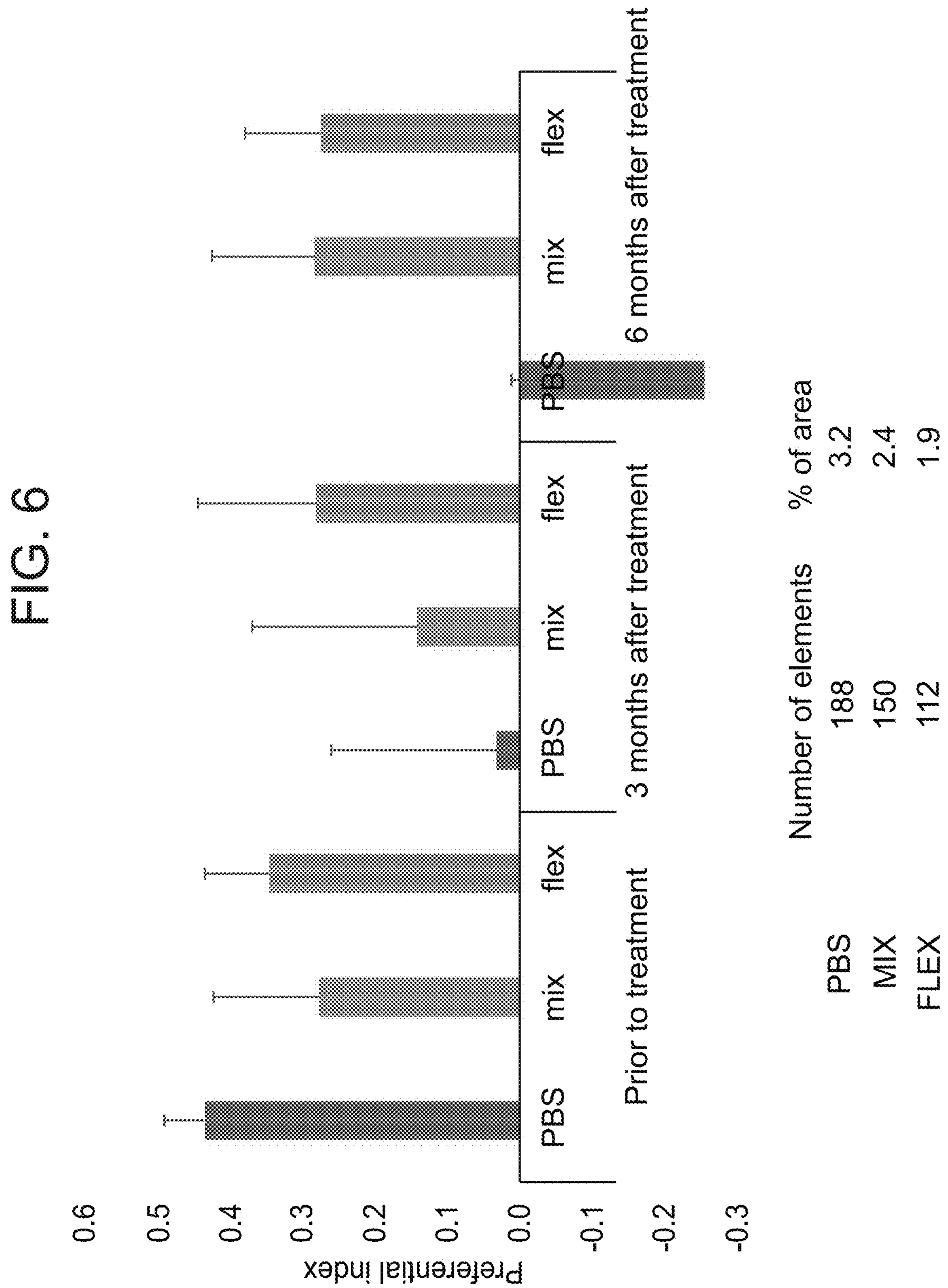

FIG. 6 is a graph which summarizes the results of a Y maze behavior test using an APP1 peptide flexibly linked to a Tau peptide as compared with PBS.

DESCRIPTION OF SPECIFIC EMBODIMENTS OF THE INVENTION

The present invention, in some embodiments thereof, relates to a method of treating Alzheimer's Disease by preventing the association of amyloid precursor protein (APP) with Tau protein.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Alzheimer disease is a multifaceted disorder that is associated with several protein-protein interactions. These include the Aß self-aggregates resulting in amyloid plaques, as well as self-aggregates of Tau, resulting in neurofibrillary tangles.

The present inventors have now confirmed that there is an interaction between APP and Tau (FIGS. 1A-C). To predict the sites through which these two proteins interact with each other, a computer-assisted methodology using BLASTP program was used. In order to confirm the presence of this interaction, a more direct, experimental approach was used involving the crosslinking of the two proteins, followed by enzymatic digestion of the conjugate and identification of the fragments that consist of sequences from both proteins.

Four peptides were selected for analysis (SEQ ID NOs: 1-4). Each were tested in direct binding experiments as well as for their ability to inhibit APP binding to TAU. The results of the dot-blot assay (as illustrated in FIG. 2A) show that only two peptides bind to each other APP1 (SEQ ID NO: 1)+Tau1 (SEQ ID NO: 3). Using an enzyme-linked immunoabsorbent assay (ELISA), the present inventors showed that a significant, but partial inhibition of the complex was seen with APP1. Furthermore, the combination of APP1 (SEQ ID NO: 1) and Tau1 (SEQ ID NO: 3), had a greater inhibitory effect on the binding of the two proteins (FIG. 2B).

Whilst further reducing the present invention to practice, the present inventors next showed that the combination of APP1 and Tau1 peptides brought about a therapeutic effect in an animal model of AD. Specifically, in FT mice treated with the APP1+Tau1 peptide mixture, an initial reduction in cognitive function was observed, followed by a gradual reversal of this effect, resulting in a full recovery of cognitive function, comparable to control non-transgenic mice of the same age at the end of the treatment course (FIGS. 3A-C). Furthermore, plaque formation representing insoluble Aß, as well as soluble Aß 1-42 load in their brains was drastically reduced in the treated mice compared to the PBS treated controls (FIGS. 4A-D and 5A-C).

Since these effects were attained when treatment was initiated either at an early age (three months), or at the age of six months, when severe cognitive functions and plaque load are already evident, the present inventors propose that agents capable of preventing the binding of APP with Tau may serve as useful therapeutics for both prevention and treatment of AD.

Thus, according to a first aspect of the present invention, there is provided a method of treating Alzheimer's Disease in a subject in need thereof comprising administering to the subject a therapeutically effective amount of an agent which prevents the binding of amyloid precursor protein (APP) to Tau protein, thereby treating the Alzheimer's Disease.

Alzheimer's disease (AD) is a progressive degenerative disease of the brain primarily associated with aging. There also exists a hereditary form called familial Alzheimer's disease (FAD). The non-hereditary form of Alzheimer which is associated with aging is also called sporadic Alzheimer. In the following the term "Alzheimer's disease" or "AD" also encompasses said hereditary form. Clinical presentation of AD is characterized by loss of memory, cognition, reasoning, judgement, and orientation. As the disease progresses, motor, sensory, and linguistic abilities are also affected until there is global impairment of multiple cognitive functions. These cognitive losses occur gradually, but typically lead to severe impairment and death in the range of four to twelve years.

Alzheimer's disease is characterized by two major pathologic observations in the brain: neurofibrillary tangles (NFT) and beta amyloid (or neuritic) plaques, comprised predominantly of an aggregate of a peptide fragment known as amyloid β. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

According to a particular embodiment the Alzheimer's disease of this aspect of the present invention is characterized by a mutation in the APP protein and/or the Tau protein, as further described herein below.

Amyloid precursor protein" ("APP") is an integral membrane protein that is expressed in tissues and concentrated in the synapses of neurons. The term "APP" encompasses all isoforms of APP. In one embodiment, the APP is the human APP. Exemplary APP isoforms include, but are not limited to, APP695, the 695 amino acid splice variant of APP (see GenBank accession no. Y00264), APP751, the 751 amino acid splice variant of APP, and APP770 (SEQ ID NO:7), the 770 amino acid splice variant of APP.

Other isoforms of APP include APP714, L-APP752, L-APP733, L-APP696, L-APP677, APP563 and APP365.

The APP of this aspect of the present invention may be one which comprises a mutation found in familial AD and other amyloidosis conditions. For example, these mutations include, but are not limited to, the Swedish double mutation (Lys670Asn, Met671 Leu); the London mutation (Val717Ile); the Indiana mutation (Val717Leu); naturally occurring mutations including Val717Phe, Val717Gly, Ala713Thr, and Ala713Val; the Austrian mutation (Thr714Ile); the Iranian mutation (Thr714Ala); the French mutation (Val715Met); the German mutation (Val715Ala); the Florida mutation (Ile716Val); the Australian mutation (Leu723Pro); the Flemish mutation (Ala692Gly); the Dutch mutation (Glu693Gln); the Arctic mutation (Glu693Gly); the Italian mutation (Glu693Lys); the Iowa mutation (Asp694Asn); and the amyloidosis-Dutch type mutation (Glu693Gln). (All numbering herein is relative to the APP770 form).

The term "Tau protein" as used herein refers to a protein of the microtubule-associated tau protein family. Members of the tau family share the common features of a characteristic N-terminal segment, sequences of approximately 50 amino acids inserted in the N-terminal segment, a characteristic tandem repeat region consisting of 3 or 4 tandem repeats of 31-32 amino acids, and a C-terminal tail. Tau proteins of the subject invention may be in a form of soluble tau intermediates, functional, aberrant, abnormally-truncated, mis-folded or mis-processed tau, and phosphorylated tau.

Preferably, the Tau protein of the present invention is of mammalian origin, more preferably, of human origin. Specifically, tau proteins of the present invention include microtubule-associated protein translated from the human chromosomal sequence of GenBank Accession No. AH005895 and naturally-occurring mammalian variants or isoforms thereof. Six human brain tau isoforms are currently known, including tau352 (GenBank Accession No. NP_058525), tau441 (GenBank Accession No. NP_005901 (SEQ ID NO:8); tau383 (GenBank Accession No. NP_058518), tau758 (GenBank Accession No. NP_058519), tau776 (GenBank Accession No. NP_001116538), and tau412 (GenBank Accession No. NP_001116539).

The Tau protein of this aspect of the present invention may be one which comprises a mutation found in familial AD and other amyloidosis conditions. For example, these mutations include, but are not limited to G272V, P301L, V337M, and R406W.

As mentioned, the present invention proposes treatment of AD using agents which are capable of preventing the binding of amyloid precursor protein (APP) to Tau protein.

According to a particular embodiment, the binding between APP and Tau protein is covalent.

According to a particular embodiment, the binding (e.g. covalent binding) is between lysine 370 of said APP (according to the numbering as set forth in SEQ ID NO: 7) and lysine 387 on said Tau protein (according to the numbering as set forth in SEQ ID NO: 8).

The agents of this aspect of the present invention are capable of preventing the binding of APP with Tau, essentially decreasing the amount of APP-Tau complex by at least 10%, 20%, 30%, 40%, 50%, 60%, 70%, 80%, 90% or more.

According to a particular embodiment, the agent is not one which affects the level of expression of either APP or Tau.

According to another particular embodiment, the agent is not a polynucleotide agent.

In one embodiment, the agent is a peptide agent.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)—CO—), ester bonds (—C(=O)—O—), ketomethylene bonds (—CO—CH2—), sulfinylmethylene bonds (—S(=O)—CH2—), α-aza bonds (—NH—N(R)—CO—), wherein R is any alkyl (e.g., methyl), amine bonds (—CH2—NH—), sulfide bonds (—CH2—S—), ethylene bonds (—CH2—CH2—), hydroxyethylene bonds (—CH(OH)—CH2—), thioamide bonds (—CS—NH—), olefinic double bonds (—CH=CH—), fluorinated olefinic double bonds (—CF=CH—), retro amide bonds (—NH—CO—), peptide derivatives (—N(R)—CH2—CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |

TABLE 2-continued

| Non-conventional amino acid | Code | Non-conventional amino acid | Code |
|---|---|---|---|
| D-serine | Dser | N-(1-hydroxyethyl)glycine | Nthr |
| D-threonine | Dthr | N-(3-indolylethyl)glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylomithine | Dnmorn | L-N-methylomithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyelopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | DmIle | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylomithine | Dmorn | L-α-methylomithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyro sine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobuty rate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl)carbamylmethyl-glycine | Nnbhm |
| N-(3,3-diphenylpropyl)glycine | Nbhe | N-(N-(3,3-diphenylpropyl)carbamylmethyl-glycine | Nnbhe |
| 1-carboxy-1-(2,2-diphenylethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclicization does not severely interfere with peptide characteristics, cyclic forms of the peptide can also be utilized.

Since the present peptides are preferably utilized in therapeutics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

The peptides of some embodiments of the invention are preferably utilized in a linear form, although it will be appreciated that in cases where cyclization does not severely interfere with peptide characteristics, cyclic forms of the peptide can also be utilized.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

Contemplated peptides may be those derived from the APP protein and/or the Tau protein.

Thus, according to one embodiment, the peptide comprises at least 10, at least 11, at least 12, at least 13, at least 14, at least 15, at least 16, at least 17, at least 18, at least 19, at least 20, at least 21, at least 22 or all of consecutive amino acids of SEQ ID NO: 1 (derived from the APP protein).

In one embodiment, the peptide comprises the amino acid sequence as set forth in SEQ ID NO: 1.

Optionally, the peptide comprises at least 10, at least 11, at least 12, at least 13, at least 14, at least 15, at least 16, at least 17, at least 18, at least 19, at least 20, at least 21, at least 22 or all of consecutive amino acids of SEQ ID NO: 1 (derived from the APP protein) and further comprises at least 10, at least 11, at least 12, at least 13, at least 14, at least 15, or all the consecutive amino acids of SEQ ID NO: 3 (derived from Tau protein).

The APP derived peptide and the Tau derived peptide may be attached via a linking moiety.

Thus, for example the APP derived peptide and the Tau derived peptide may be crosslinked using a crosslinker that crosslinks lysine residues (e.g. using BS3).

Examples of linking moieties include but are not limited to a simple covalent bond, a flexible peptide linker, a disulfide bridge or a polymer such as polyethylene glycol (PEG). Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by addition of cysteine residues, as further described herein below. Linking through polyethylene glycols (PEG) can be achieved by reaction of monomers having free cysteines with multifunctional PEGs, such as linear bis-maleimide PEGs. Alternatively, linking can be performed though the glycans on the monomer after their oxidation to aldehyde form and using multifunctional PEGs containing aldehyde-reactive groups.

An example of a flexible peptide linker is GGGGSGGGGSGGGGS (SEQ ID NO: 12).

An example of a peptide which comprises an APP derived peptide linked by a flexible peptide linker to a TAU derived peptide is:

```
                                              SEQ ID NO: 13
HFQKAKERLEAKHRERMSQVMREGGGGSGGGGSGGGGSGLGDRKDQGGY
TMHQD.
```

An example of a rigid peptide linker is EAAAKEAAAKEAAAK (SEQ ID NO: 14).

An example of a peptide which comprises an APP derived peptide linked by a rigid peptide linker to a TAU derived peptide is:

```
                                            (SEQ ID NO: 15)
HFQKAKERLEAKHRERMSQVMREEAAAKEAAAKEAAAKGLGDRKDQGGY
TMHQD.
```

Selection of the position of the link between the two peptides should take into account that the link should not substantially interfere with the ability of the full length molecule to prevent binding of APP protein to Tau protein.

Thus, for example, the linking moiety is optionally a moiety which is covalently attached to a side chain, an N-terminus or a C-terminus of the APP peptide, as well as to a side chain, an N-terminus or a C-terminus of the Tau derived peptide.

Preferably the linking moiety is attached to the C-terminus of APP derived peptide, and to the C-terminus of Tau derived peptide.

As mentioned, the linking moiety may be a cysteine residue.

Thus, in some embodiments of the invention, each of the peptides comprise at least one cysteine residue, and the peptides are covalently linked to one another via a disulfide bridge formed between a cysteine residue in the APP derived peptide and a cysteine residue in the Tau derived peptide.

Typically, the cysteine is situated at the carboxy end of the peptide monomers.

Herein throughout, the phrases "disulfide bridge" and "disulfide bond" are used interchangeably, and describe a —S—S— bond.

The linker may comprise additional amino acids linked together by peptide bonds which serve as spacers such that the linker does not interfere with the biological activity of the final compound. The linker is preferably made up of amino acids linked together by peptide bonds. Thus, in preferred embodiments, the linker is made up of from 1 to 10 amino acids linked by peptide bonds, wherein the amino acids are selected from the 20 naturally occurring amino acids. Some of these amino acids may be glycosylated, as is well understood by those in the art. In a more preferred embodiment, besides cysteine the amino acids in the linker are selected from glycine, alanine, proline, asparagine, glutamine, and lysine. Even more preferably, besides cysteine, the linker is made up of a majority of amino acids that are sterically unhindered, such as glycine and alanine.

Such exemplary peptides which comprise the APP derived peptide and the Tau derived peptide are those that comprise the sequence as set forth in SEQ ID NOs: 5 or 6 or homologs thereof.

Optionally, the agent comprises at least two peptides, the first comprising at least 10, at least 11, at least 12, at least 13, at least 14, at least 15, at least 16, at least 17, at least 18, at least 19, at least 20, at least 21, at least 22 or all of consecutive amino acids of SEQ ID NO: 1 (derived from the APP protein); and the second comprising at least 10, at least 11, at least 12, at least 13, at least 14, at least 15, or all the consecutive amino acids of SEQ ID NO: 3 (derived from Tau protein).

The peptide may be a homolog having at least 90%, 91%, 92%, 93%, 94%, 95%, 96%, 97%, 98% or even 99% identity with SEQ ID NO: 1 and/or 3.

The peptide may be a homolog having at least 90%, 91%, 92%, 93%, 94%, 95%, 96%, 97%, 98% or even 99% identity with SEQ ID NO: 5 or 6.

In place of the word "identity", the terms "homologous" or "homology" are used synonymously in the present description. The identity between two nucleic acid sequences or polypeptide sequences may be calculated by comparison with the BESTFIT program based on the algorithm of Smith, T. F. and Waterman, M. S (Adv. Appl. Math. 2: 482-489 (1981)) setting the following parameters for amino acids: Gap creation penalty: 8 and Gap extension penalty: 2; and the following parameters for nucleic acids: Gap creation penalty: 50 and Gap extension penalty: 3. Preferably, the identity between two nucleic acid sequences or polypeptide sequences is defined by the identity of the nucleic acid sequence/polypeptide sequence respectively over the entire sequence length, which is calculated by comparison using the GAP program based on the algorithm of Needleman, S. B. and Wunsch, C. D. (J. Mol. Biol. 48: 443-453) setting the following parameters for amino acids: Gap creation penalty: 8 and Gap extension penalty: 2; and the following parameters for nucleic acids: Gap creation penalty: 50 and Gap extension penalty: 3.

In the context of the present invention, two amino acid sequences are identical if they have the same amino acid sequence.

In one variant, homologs are understood to mean the corresponding retro-inverso sequences of the monomers mentioned above. The term "retro-inverso sequence", in accordance with the invention, refers to an amino acid sequence which is composed of amino acids in the enantiomeric form (inverso: chirality of the alpha-carbon atom inverted) and in which the sequence order has also been reversed compared to the original amino acid sequence (retro=backwards).

In a further variant, the peptides according to the invention have sequences which differ from the specified sequences by up to three amino acids.

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(-CH.sub.2).sub.5-COOH]—CO— for aspartic acid. Those non-conservative substitutions which fall under the scope of the present invention are those which still constitute a peptide having anti-bacterial properties.

As mentioned, the N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO-, n-propyl-CO-, iso-propyl-CO-, n-butyl-CO-, sec-butyl-CO-, t-butyl-CO-, hexyl, lauroyl, palmitoyl, myristoyl, stearyl, oleoyl phenyl-CO-, substituted phenyl-CO-, benzyl-CO- and (substituted benzyl)-CO-. Examples of alkoxy carbonyl and aryloxy carbonyl groups include CH3—O—CO—, (ethyl)-O-CO-, n-propyl-O-CO-, iso-propyl-O-CO-, n-butyl-O-CO-, sec-butyl-O-CO-, t-butyl-O-CO-, phenyl-O-CO-, substituted phenyl-O-CO- and benzyl-O-CO-, (substituted benzyl)-O-CO-. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with -NH-.sub.2, -NHR.sub.2 and -NR.sub.2R.sub.3) or ester (i.e. the hydroxyl group at the C-terminus is replaced with -OR-.sub.2). R.sub.2 and R.sub.3 are independently an aliphatic, substituted aliphatic, benzyl, substituted benzyl, aryl or a substituted aryl group. In addition, taken together with the nitrogen atom, R.sub.2 and R.sub.3 can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include -NH.sub.2, -NHCH-.sub.3, -N(CH.sub.3).sub.2, -NH(ethyl), -N(ethyl).sub.2, -N(methyl) (ethyl), -NH(benzyl), -N(C1-C4 alkyl)(benzyl), -NH(phenyl), -N(C1-C4 alkyl) (phenyl), -OCH.sub.3, -O-(ethyl), -O-(n-propyl), -O-(n-butyl), -O-(iso-propyl), -O-(sec-butyl), -O-(t-butyl), -O-benzyl and -O-phenyl.

The peptides of the present invention may be attached (either covalently or non-covalently) to a penetrating agent.

As used herein the phrase "penetrating agent" refers to an agent which enhances translocation of any of the attached peptide across a cell membrane. According to one embodiment, the penetrating agent is a peptide and is attached to the peptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

Examples of peptide penetrating agents include those set forth in SEQ ID NOs: 9-11. By way of non-limiting example, cell penetrating peptide (CPP) sequences may be used in order to enhance intracellular penetration. CPPs may include short and long versions of TAT (YGRKKRR-SEQ ID NO: 9 and YGRKKRRQRRR-SEQ ID NO: 10) and PTD (RRQRR-SEQ ID NO: 11). However, the disclosure is not so limited, and any suitable penetrating agent may be used, as known by those of skill in the art.

According to a particular embodiment, the peptides of the present invention (which are derived from either APP or Tau) are no longer than 30, 31, 32, 33, 34, 35, 36, 37, 38, 39 or 40 amino acids (this includes the APP or Tau related peptide together with any additional attached sequence, such as a cell penetrating peptide as described above).

According to a particular embodiment, the peptides of the present invention (which are derived from both APP or Tau) are no longer than 70, 71, 72, 73, 74, 75, 76, 77, 78, 79 or 80 amino acids (this includes the APP and Tau related peptide together with any additional attached sequence, such as a cell penetrating peptide as described above and/or linker sequence).

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

According to another aspect, the agent is one that decreases the amount of the APP-Tau complex to a greater extent than it decreases the amount of the non-complexed APP or Tau. Thus, the agent may be an antibody which specifically binds to the APP-Tau complex and does not bind to the App or Tau protein when it is not present in the complex (i.e. it binds with at least 2 fold, 3 fold, 4 fold, 5 fold, 6 fold, 7 fold, 8 fold, 9 fold, 10 fold higher affinity to the complex than to the non-complexed proteins).

The peptides of the present invention may be provided per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agents (e.g. peptides) accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to a particular embodiment, the administration is intranasal.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (peptides) effective to prevent, alleviate or ameliorate symptoms of a disorder (e.g., Alzheimer's Disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to brain or blood levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Methods of identifying novel agents which are useful for treating Alzheimer's Disease (AD) are also disclosed. The method comprises analyzing the amount of a complex comprising amyloid precursor protein (APP) covalently bound to Tau protein in the presence of said agent, wherein a downregulation in the amount (e.g. a down-regulation of at least 10%, 20%, 30%, 40%, 50%, 60%, 70%, 80%, 90% or more) of said complex in the presence of said agent compared to the amount of said complex in the absence of said agent is indicative of an agent useful for treating Alzheimer's Disease (AD).

Examples of agents which can be analyzed include peptides, small molecules, antibodies and polynucleotide agents.

The complex which is analyzed may comprise an APP protein which is covalently bound on lysine 370 thereof to lysine 387 on a Tau protein. The covalent binding may be carried out using a crosslinker that crosslinks lysine residues (e.g. BS 3 (bis(sulfosuccinimidyl)suberate. Other exemplary crosslinkers include but are not limited to DSS (disuccinimidylsuberate), DSP (dithiobis(succinimidylpropionate)), DMTMM (4-(4,6-dimethoxy-1,3,5-triazin-2-yl)-4-methylmorpholinium chloride) with and without PDH (pimelic acid dihydrazide), sulfo-SDA (sulfosuccinimidyl 4,4'-azipentanoate), CBSS (carboxybenzophenone sulfosuccinimide), DSSO (disuccinimidylsulfoxide), DSBU (disuccinimidyldibutyric urea), BDP-NHP (N-hydroxyphthalamide ester of biotin aspartate proline), CBDPS (cyanurbiotindimercaptopropionyl succinimide), DC4 (1,4-bis(4-((2,5-dioxopyrrolidin-1-yl)oxy)-4-oxobutyl)-1,4-diazabicyclo[2.2.2]octane-1,4-diium), and MC4 (N,N'-bis(4-((2,5-dioxopyrrolidin-1-yl)oxy)-4-oxobutyl)-morpholine).

As used herein the term "about" refers to +/−10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition. According to one embodiment, the method is for preventing of delaying the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

As used herein the term "about" refers to±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Chemicals and Antibodies:

Recombinant human APP770, Recombinant human APP770-His tag, Recombinant human Tau-441 (2N4R) and purified anti amyloid 1-16 (SIG-39320) were all purchased from Bio-Legend US. Anti Tau antibodies (anti Tau pantropic, at-5004) was purchased from MBL, US. Anti-mouse HRP was from Jackson US. Mouse anti-glyceraldehyde 3-phosphate dehydrogenase antibody (GAPDH) Cat# MAB374 purchased from Milipore. Fluorescein or rhodamine isothiocyanate were purchased from (Sigma-Aldrich). Bis-SulfoSuccinimidylSuberate cross-linker (BS3-H12/D12) was from Creative Molecules Inc. Protein A/G agarose beads (Santa Cruz US).

Mouse lines: The 5×FAD double transgenic mice (Tg6799 line APP/PS1), (JAX), co-express the human amyloid precursor protein carrying five familial Alzheimer's disease mutations: the Swedish, Florida and London mutations and two mutations of the human presenilin-1 (30). The DM hTau transgenic mouse line expressing two mutations was also used. All mouse lines were maintained on a C57Bl/6 background. Heterozygous 5×FAD Tg mice were used for crossing with DM hTau heterozygous Tg mice to produce double Tg mice 5×FAD×Tau (FT). Genotyping was performed by PCR amplification of tail DNA (35). The mice were housed in individually ventilated cages (no more than 5 mice per cage) in a temperature-controlled facility with a 12-h light/dark cycle. Animal weight was 20-25 g and mice were given food and water ad libitum.

Western Blot Analysis of APP and Tau Protein Binding:

Western blot was performed as previously described (36). Loaded samples were prepared as follows: Anti His antibodies (1-2 μg) were bound to protein A beads (10 μl) in a microfuge for one hour at room temperature (RT). Beads were washed with phosphate buffered saline (PBS) containing only 50 mM NaCl (which was used all along for washes), centrifuged and supernatant (sup) aspirated. APP-His (1 μg) was added and incubated for one hour at RT and the complex was washed again, centrifuged and the sup aspirated. Tau protein (1 μg) was added for a one hour incubation at RT. As a negative control, Tau protein was added to protein A beads, incubated overnight (ON) at 4° C. Before loading, samples were centrifuged, sup aspirated and 80 μl PBS +20 μl loading buffer (5×) was added. Samples were boiled, centrifuged and 20 μl of each sample was loaded as well as 50 ng in 20 μl of either APP protein or Tau protein. For electrophoretic separations, 10% polyacrylamide gels were used and transferred to nitrocellulose membranes. The membranes were blocked with PBS 5% bovine serum albumin (BSA) for 1 h, then washed with 0.05% Tween in tris buffered saline (TBST) and reacted with either anti Aβ antibodies (6E10 1:250 dilution) or anti Tau antibodies (anti Tau, 1:2500 dilution) ON at 4° C. The membranes were washed three times with PBS-Tween (0.05%) and reacted with secondary anti-mouse HRP (1:10,000) for 1 h at RT. The membranes were washed with TBST, reacted with electrochemiluminescence (ECL) and measured using the Amersham Imager 600UV (GE Life Technologies). Mouse anti-glyceraldehyde 3-phosphate dehydrogenase antibody (1:10,000) was used as a loading control.

Computing-Based Approach for Predicting and Design of APP and Tau Peptides:

The hypothesis is that Tau binds to APP. Therefore, for each protein, putative binding proteins were searched using UNIPROT (20), a protein based search under GO molecular function section. For each protein sequence result, a BLAST (basic local alignment search tool) search was executed against the other binder proteins.

GSK3 is one of the proteins that Tau interacts with (based on the paper "Linking Aß and Tau in Late-Onset Alzheimer's Disease: A Dual Pathway Hypothesis") (37). Running a local sequence protein alignment (BLAST) between GSK3 and APP, a short sequence of ~20 amino acids was found to align. Hence, this sequence might be the starting point for peptide design to bind with Tau. The opposite analysis gave a common sequence on Tau FKB1A and CD74. Using the BLASTP program, areas in both APP and Tau protein were identified as possible candidates for the requested binding peptides. Apparently, both GSK3 and ApoE3 interact with the same location on APP, and the microtubule associated protein is a candidate area on the Tau protein (38). The second Tau peptide which was selected is from the N-terminus of the protein, as this region of Tau is adjacent to phopspho-Tyr18-Tau, which has been found to accompany disease progression of Alzheimer's disease and Tauopathy (23).

Crosslinking of APP and Tau Proteins to Identify and Confirm Candidate Peptides for in Vitro/In Vivo Experiments:

A mixture of APP and Tau proteins was treated with the crosslinker BS3H12/D12. A mixture of 1 μg/10 μl of APP (575 nM final conc.) and 0.5 μg/10 ul of Tau (545 nM final conc.) was kept overnight at 4° C. The next day, 1 μl of BS3 (50 μM final conc.) was added to the mixture for 1 h incubation at 37° C. The reaction was stopped by adding 1 μl of 2M Tris, pH 8.4.

A sample of the reaction was checked by Western blot for verification of APP and Tau binding and the rest of the material was processed for LC-MS/MS. BS3 is a linear molecule which forms a covalent bridge, a crosslink between two lysine side chains. Only lysine residues that are close to each other can be crosslinked since the length of the crosslinker is about 30 A. The APP-Tau complex has two lysine residues, one on each protein, which are close enough to each other and therefore can be crosslinked. The lysine residues which were crosslinked were identified by performing LC-MS/MS and using the appropriate software. The crosslinks were identified with the stand-alone version 2.1.1 of xQuest (39, 40). Most of the identified crosslinks were between lysine residues on the same protein. Only one crosslink was identified between APP and Tau.

Synthetic Peptides:

Four synthetic peptides, two from APP protein (APP1 and APP2) and two from Tau protein (Tau1 and Tau2) were prepared by GL Biochem (Shanghai, China) Ltd.

```
APP 1:
                              SEQ ID NO: 1
HFQKAKERLEAKHRERMSQVMRE

APP 2:
                              SEQ ID NO: 2
ATVIVITLVMLKKKQYTS

Tau1:
                              SEQ ID NO: 3
GLGDRKDQGGYTMHQD

Tau2:
                              SEQ ID NO: 4
KPGGGQVEVKSEKLDFK
```

In Vitro Tests:

Inhibition of Tau and APP Proteins Binding by Peptides APP1, APP2, Tau1, Tau2 and their Combinations:

An ELISA plate (96 wells) was coated with Tau protein 1 μg/ml in bicarbonate PH=8.2 50 μl/well, then incubated overnight at 4° C. Peptides and their combinations were also incubated overnight at 4° C. in PBS 1 μg/ml. The next day, the plate was washed 3× with PBS and blocked with 3% BSA/PBS for two hours at RT. The plate was washed again 3× with PBS and peptides or their combinations 50 ul/well were added for four hours at RT. The plate was washed again 3× with PBS and APP protein, 1 μg/ml 50 μl/well was added for ON incubation at 4° C. The next day, the plate was washed 3× with PBS, following which anti Aß 1-16 (1 mg/ml) was added (1:500 dilution 50 μl/well) for two hours at RT. The plate was washed again and anti-mouse HRP antibodies (1:10,000 dilution in PBS 1% BSA) added at 50 μl/well. Color reaction was stopped with 50 μl/well of 1M H2S04 and read at 0.D. 450.

Peptide Labeling with Fluorescein and Rhodamine for Visualization of Peptide Binding:

The peptides APP1, APP2, Tau-1 and Tau-2 were labeled with fluorescein or rhodamine. The labelling was done according to the manufacturer's instructions and methods in Cell Biology Protein labeling with fluorescent probes (41). Five mg of each peptide was dissolved in 0.1M sodium carbonate pH 9.0 (1 ml) and fluorescein or rhodamine-isothiocyanate (2 mg in 0.1 ml DMF or DMSO) was added. The reaction mixture was stirred at RT for 1 h and moved for overnight incubation to 4° C. in the dark. The possible remaining fluorescein or rhodamine was quenched with ammonium chloride for 2 h at room temperature.

Each of the four labeled peptides was blotted on a nitrocellulose membrane applying similar concentrations and labels to each sample. The following mixture of the labeled APP and Tau peptides: APP1F+Tau-1R, App1F+Tau-2R, APP2F+Tau-1R, APP2F+Tau-2R, (fluorescein green F, rhodamine red R) were also applied to the nitrocellulose membrane. The expectation was that only actual binding between the green and red labelled peptides will yield a yellow color.

Histological Staining and Quantitation of Amyloid:

Mice were sacrificed (trans-cardially punctured, and saline-perfused). The right brain hemisphere of each mouse was stored at −70° C. to quantify Aβ levels. The left hemispheres were fixed (4% paraformaldehyde) and prepared for paraffin blocks which were cut into six micron sagittal sections and used for histological staining and examination. Sagittal brain sections were stained with Congo red dye (Sigma-Aldrich) and visualized by fluorescence microscopy. Quantification of amyloid depositions was done for the whole hippocampal area in a blinded fashion using Imaging Research software from the National Institutes of Health in an unbiased stereological approach.

Analysis of Amyloid Peptide from Brain Homogenate Samples:

The right hemisphere of each mouse in each treatment group was homogenized with PBS containing protease inhibitors and centrifuged at 40,000 g for 40 minutes. The supernatant-containing soluble Aβ was aliquoted and stored at −70° C. The levels of Aβ (1-42) in the brain samples were assessed by an ELISA kit (Mercury EZHS42, US) for high sensitivity human amyloid beta-42 (42), n=5 mice/group.

In-Vivo Animal Treatment and Behavior Test:

The cross of heterozygous 5×FAD Tg mice (Tg 6799) with heterozygous DM hTau Tg yielded double Tg mice 5×FAD×Tau (FT) which were subsequently used. As controls, non Tg littermates were used. The mice were housed in individually ventilated cages in a temperature-controlled facility with a 12-h light/dark cycle. Mice were randomly assigned to groups of peptide-treatment or PBS-treated controls (3-6 animals each). A total of 16 male and 6 female mice were used in the in vivo studies. No behavioral differences were observed between the sexes when tested in the Y-maze experiment, in terms of response to treatment. Treatment, in two different experiments, started at either 3 or 6 months old mice. A mixture of APP1 peptide 5 μg/5 ul and Tau-16 peptide 5 μg/5 μl was administered nasally every second day for 4-5 months. In the control group PBS was administered similarly.

Behavioral assessments were conducted before starting the treatment and then once a month during the treatment period, a total of four or five assessment sessions. The assessments included the Y-maze test assessing spatial recognition memory, as a hallmark of cognition function (43) and the open-field (OF) test, an established anxiety and basic motor functions test (44), to control for confounding factors that may affect the behavior in the Y maze.

The Y-maze test (45) consists of two trials, first "training" and second "retention", separated by an inter-trial interval (ITI). Each arm of the Y-maze was equipped with a guillotine door that could be operated manually. The three identical arms were randomly designated as follows: the "start" (steam) arm, in which the mouse began to explore the maze (always open); the "Novel" arm, which was closed off during the first trial, but open in the second one; and the "other" arm (always open). The first (training) trial lasted five minutes and allowed the mouse to explore only two arms ("start" and "other") of the maze. Access to the third ("Novel") arm was blocked. The second trial (retention) was conducted after a two minute ITL. During this three minute trial, all three arms were accessible. The mouse was returned to the same starting arm and was allowed to explore all three arms. Retention was scored as a preferential index to the "Novel" arm, that was calculated as follows: time spent in the "Novel" arm minus the time spent in the old arm divided by the sum of time spent in both arms (46).

Additional assessments evaluated the effects of the treatment on both basic locomotor functions and anxiety using the open-field (OF) test and verified that the treatment's effect on cognition was not confounded by these factors. Open-field test assessments were performed in a dark gray circular arena (diameter 56 cm) under dim illumination (20 lux). The mice were placed in the arena for five minutes. Locomotion in the arena was quantified using the Noldus video tracking software (MediaRecorder and Ethovision).

Statistical Analysis:

The in-vivo data was analyzed by SPSS software (version 23, IBM, Armonk, N.Y.), and Statistica (version 12, Statsoft). The datasets were first tested for normality using the Shapiro-Wilks test. If the data were normally distributed, parametric comparisons were performed: one-sample or independent samples t-tests and one-way analysis of variance (ANOVA) followed by the relevant post-hoc comparisons. When the data deviated significantly from normality, non-parametric tests were applied: Mann-Whiteny U test or Kruskal-Wallis one-way ANOVA followed by Dunn's pairwise comparison post hoc analysis. Data are presented as the mean with the standard error of the mean (SEM). A probability value (p) of less than 0.05 was considered significant.

Results

Verification of APP and Tau Protein Binding and Crosslinking of the Proteins

A Western blot was performed to determine if the APP protein binds to Tau. As seen in FIG. 1A, anti Tau antibodies labelled Tau protein alone (70 kD) and Tau bound to APP beads. An additional band (55 kD) of immunoglobulin was seen in the samples that were bound to beads containing anti His antibodies. FIG. 1B has the identical loading plan as in FIG. 1A, but the blot was incubated with anti Aß antibodies (6E10) which bound to the APP protein. Here, APP, APP-His protein bound to beads or Tau bound to APP-His beads demonstrated 110 kD band which is the molecular weight (MW) of APP. FIGS. 1A and 1B confirm that the two proteins which are the main components contributing to AD bind to each other.

The proteins were then chemically crosslinked using BS3-H12/D12, and the crosslinked product of both proteins was analyzed. As shown in FIG. 1C, the anti APP antibodies labelled the band of APP protein, as well as a 180 kD band representing the crosslinked APP (110 kD) and Tau (70 kD) proteins.

Prediction of the APP and Tau Peptides Involved in the Protein Binding

Using the UNIPROT (20) and BLASTP (21) programs, areas in both the APP and Tau protein were identified as possible areas of interaction between the two proteins. Likely candidates were the location on APP that align with both GSKE3 and ApoE3, and the microtubule-associated protein region and/or the N-terminal region of Tau. Upon analysis of the crosslinked material (see FIG. 1C), which was processed for LC-MS/MS, only one crosslink was identified between APP and Tau, between lysine 370 on APP and lysine 387 on Tau. The crosslinked lysine for APP resides very close to the accordingly predicted APP1 (390-412) peptide as can be seen by a crystal structure of the region (22). A control, the APP peptide (previously reported to bind Tau (19), namely APP2 (residues 713-730) was also tested. The peptide Tau1 (residues 19-34) which is in the N-terminal end of Tau protein was tested, since phospho-Tyr-hTau was reported to accompany AD progression and Tauopathy (23). The peptide Tau2 (residues 331-348) from the microtubule area was also tested as it is proximal to the crosslinked lysine 387.

In Vitro Assessment of the Involvement of the Peptides in APP and Tau Protein Binding All four candidate peptides were labelled with fluorescein. APP1, Tau1 and Tau2 were also labelled with rhodamine for visualization of peptide binding. The dot-blot assay (FIG. 2A) shows that the only two peptides that bound to each other are APP1F+Tau1R, as seen by the yellow color. All other combinations resulted in separate red and green dots (except for a faint yellow color for the combination of APP1F and Tau2R).

The next step was to determine by an enzyme-linked immunoabsorbent assay (ELISA) which of the single peptides or mixtures inhibits APP-Tau binding. FIG. 2B shows that APP-Tau binding is not inhibited by Tau1 or APP2. A significant but partial inhibition was seen with APP1. However, the combination of APP1 and Tau1, which was the only combination shown to bind by the dot blot (FIG. 2A), had a greater inhibitory effect on the binding of the two proteins.

In Vivo Treatment of 5×FAD×Tau (FT) Mice with APP1 and Tau1 Mixture and its Effect on Cognition, Plaques and Soluble Brain Aβ 1-42 Levels APP1 and Tau1 were assessed for their in vivo effects. The animal model used was 5×FAD APP Tg mice crossed with Tau Tg mice, 5×FAD×Tau(FT). The mice were nasally treated three times per week for 4-5 months with the peptide mixture.

Cognitive Functions

The FT mice used show cognitive impairments at the age of four months. Behavioral assessments were conducted before starting the treatment, at the age of either three months (before cognitive impairment) or six months (after significant impairment was seen), and then once a month during the treatment period, for a total of four or five assessment sessions. The assessments included the Y-maze test, assessing the spatial recognition memory, as a hallmark of cognition functions, as well as an open field (OF) test, an established anxiety and basic motor functions test, controlling confounding factors that may affect behavior in the Y-maze. Control mice, were either FT mice treated with PBS or non Tg littermates treated with the mixture. At the end of the experiment, the mice were sacrificed and their brains excised. One half of the brain was prepared for histology and one half was frozen at −70° C. for measuring soluble Aß 1-42.

FIG. 3A depicts the cognitive functions, assessed in the Y-maze, of control (non-transgenic) and transgenic FT mice, treated and non-treated, compared between the ages of three to eight months. At the age of three months, the performance of the transgenic and control groups were similar, exhibiting preference to the Novel arm (Statistical significance, "0" [$t_{(3)}$=3.824; p (one-sided)=0.016], was noticed only by the non TG control).

The benefit of the treatment was evident at the end of the treatment course at eight months, when only non-treated FT mice exhibited significantly poor Y-maze performance. In addition, although ANOVA indicated no significant difference between the groups at eight months [$F_{(2)}$=3.658; p=0.064], Dunnet's post-hoc comparisons (one-sided) indicated that non-treated FT differed significantly from non-Tg control mice (p=0.048), whereas treated FT mice did not differ from non-Tg control mice (p=0.471).

FIG. 3B illustrates the cognitive functions, assessed in the Y-maze, of control (non-transgenic) and FT mice, treated and non-treated, that were compared between the ages of 6 to 10 months. At six months, only non-Tg control mice exhibited a significant preference to the Novel arm in the Y-maze [$t_{(9)}$=3.780; p (one-sided)=0.002], while non-treated FT mice performed significantly worse than non-Tg controls [$t_{(16)}$=2.198; p (one-sided)=0.022] and did not exhibit a significant differential preference to the Novel arm [$t_{(7)}$ =0.508; p (one-sided)=0.314].

Kruskal-Wallis analysis indicated a significant age-associated cognitive decline only among non-treated FT mice between six to eight months. Dan's post-hoc comparisons indicated that eight months old non-treated FT mice performed significantly worse than six months old non-treated FT mice (p=0.029). In addition, eight months old non-treated FT mice exhibited a significant negative differential preference to the Novel arm, i.e. <"0". ANOVA indicated no significant differences in FT treated mice over four months of treatment, the benefits of treatment were evident at the end of the course. At the age of 10 months, only treated FT mice exhibited a significant (#P=0.024) differential preference to the Novel arm. FIG. 3C summarizes the cognitive performance (preferential index) obtained from 10 months old FT mice nasally treated for four months with the APP1 and Tau1 peptide mixture, indicating the significant effect of the treatment.

The results of the open field (OF) tests, did not show any differences in anxiety throughout the five-month course of treatment between control (treated) non-Tg and treated FT mice. In addition, the groups did not differ substantially in their motor functions. The maximal walking velocity was similar in four out the five months course of treatment (results not shown). Therefore, the treatment's effect on cognition was not confounded by locomotor functions or anxiety.

To address the issue of an association between amyloid plaques and cognitive decline, both insoluble Aß (represented by plaques) and soluble Aß were measured in the brain. The mice were sacrificed at the end of the experiment and their brains excised to quantify the percentage of brain area in which plaques were present.

Figure 4A:
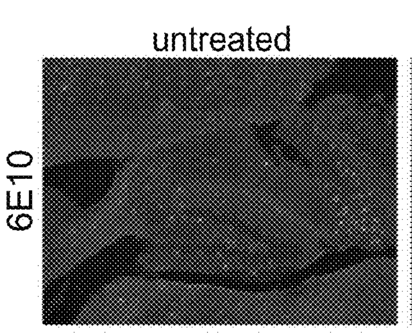
Figure 4B:
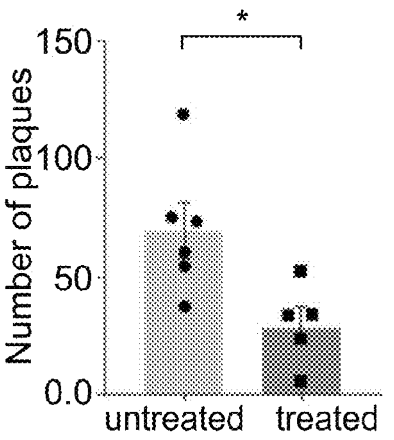
Figure 4C:
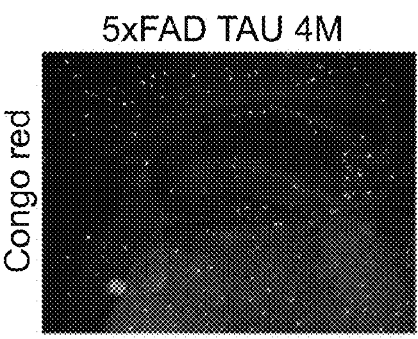
Figure 4C:
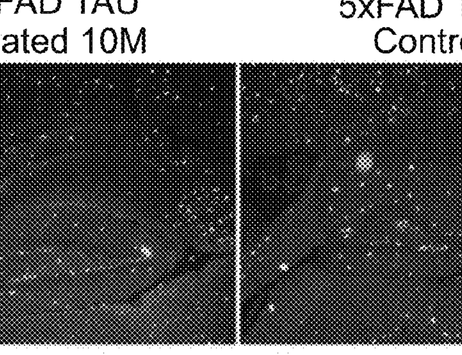
Figure 4D:
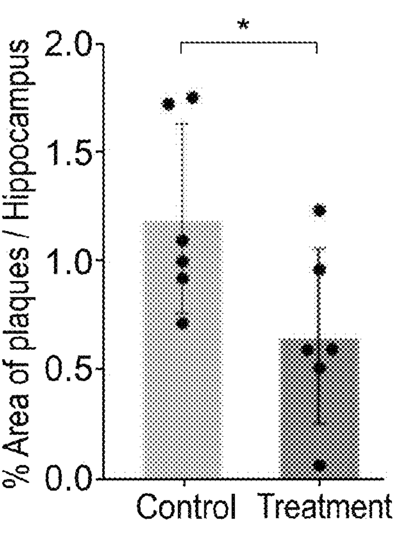

Sagittal brain sections were stained with either anti-Aß 6E10 antibody (FIG. 4A) or Congo red dye (FIG. 4C). Quantification of Aß depositions was done for the hippocampus area in a blinded fashion using Imaging Research software from National Institutes of Health in an unbiased stereological approach. For Congo red, the results presented are percentage of area of congophilic staining versus total area of measured hippocampus. For 6E10 staining, the results are presented as number of positive staining per total hippocampus region (FIG. 4B), indicating significant reduction as the result of treatment. At the age of ten months, the % plaque area in FT mice treated with the APP1+Tau1 peptide mixture was significantly reduced (FIG. 4C, middle panel), a substantial reduction of more than 45% as compared with the non-treated FT mice. In addition, staining sections of brains with 6E10 anti-A_antibodies of untreated 10 months old mice revealed a significantly higher number of plaques than the same age treated mice (FIG. 4A,B).

In 5×FAD mice treated with APP1+Tau1 peptide mixture for 5 months, the majority of the mice at 8 months of age showed, as did the FT mice, an increased preferential index as compared to PBS treated 5×FAD mice, indicating the significance of the treatment (FIG. 5A P=0.0344). However, no reduction in the plaque load was observed in brains of the treated 5×FAD APP mice (FIG. 5B), and hence no correlation with cognitive function.

Figure 4E:
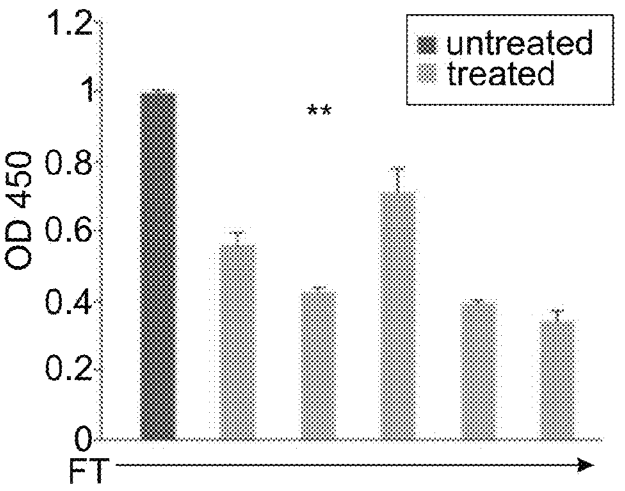

Recently, the soluble Aß has become the focus of AD research and was suggested to contribute to AD development (Esparza et al., 2016). Therefore, the content of soluble Aß 1-42 was assessed by ELISA in the brains. Soluble Aß 1-42 was significantly lower in the brains of the peptide treated mice, in both FT and 5×FAD, than in the control (PBS) treated mice (FIGS. 4E and 5C p<0.006).

The results of the open field (OF) tests, did not show any differences in anxiety throughout the five-month course of treatment between control non-Tg and treated FT or 5×FAD mice. In addition, the groups did not differ substantially in their motor functions. The maximal walking velocity was similar in four out the five months course of treatment (results not shown). Hence, the effect of treatment on cognition was not confounded by locomotor functions or anxiety.

An additional experiment was carried out testing the effects of the APP1 peptide flexibly linked to the TAU peptide on behavior as tested in the Y maze. The results are provided in FIG. 6. The flexible peptide has the following sequence:

```
                                          SEQ ID NO: 13
HFQKAKERLEAKHRERMSQVMREGGGGSGGGGSGGGGSGLGDRKDQGGY
TMHQD.
```

As can be seen from FIG. 6, the control treated mice (PBS) decline in their preferential index (cognitive ability) while the treated mice improve.

The number of elements and % of area in the hippocampus are summarized in Table 3, herein below.

TABLE 3

| | Number of elements | % of area |
|---|---|---|
| PBS | 188 | 3.2 |
| MIX | 150 | 2.4 |
| FLEX | 112 | 1.9 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Ben-Yedidia T & Arnon R (2005) Towards an epitope-based human vaccine for influenza. *Human Vaccines* 1(3):95-101.
2. Lowell G H, Ziv S, Bruzil S, Babecoff R, & Ben-Yedidia T (2017) Back to the future: immunization with M-001 prior to trivalent influenza vaccine in 2011/12 enhanced protective immune responses against 2014/15 epidemic strain. *Vaccine* 35(5):713-715.
3. Sandomenico A, et al. (2009) Protein-Protein Interactions: A Simple Strategy to Identify Binding Sites and Peptide Antagonists. *Chemical biology & drug design* 73(5):483-493.
4. Sela M & Arnon R (1960) Studies on the chemical basis of the antigenicity of proteins. 1. Antigenicity of polypeptidyl gelatins. *Biochemical Journal* 75(1):91.
5. Arnon R & Sela M (1960) Studies on the chemical basis of the antigenicity of proteins. 2. Antigenic specificity of polytyrosyl gelatins. *Biochemical Journal* 75(1):103.
6. Arnon R, Maron E, Sela M, & Anfinsen C B (1971) Antibodies reactive with native lysozyme elicited by a completely synthetic antigen. *Proceedings of the National Academy of Sciences* 68(7):1450-1455.
7. Geiger B & Arnon R (1974) Immunogenicity and antigenic specificity of the loop fragment of lysozyme. *European journal of immunology* 4(9):632-634.
8. Teitelbaum D, Meshorer A, Hirshfeld T, Arnon R, & Sela M (1971) Suppression of experimental allergic encephalomyelitis by a synthetic polypeptide. *European journal of immunology* 1(4):242-248.
9. Teitelbaum D, Fridkis-Hareli M, Arnon R, & Sela M (1996) Copolymer 1 inhibits chronic relapsing experimental allergic encephalomyelitis induced by proteolipid protein (PLP) peptides in mice and interferes with PLP-specific T cell responses. *Journal of neuroimmunology* 64(2):209-217.
10. Langbeheim H, Arnon R, & Sela M (1978) Antiviral effect on MS-2 coliphage obtained with a synthetic antigen. *Proceedings of the National Academy of Sciences* 73(12):4636-4640.
11. Langbeheim H, Teitelbaum D, & Arnon R (1978) Cellular immune response toward MS-2 phage and a synthetic fragment of its coat protein. *Cellular immunology* 38(1):193-197.
12. Apostolova L G (2016) Alzheimer Disease. *Continuum (Minneap Minn)* 22(2 Dementia):419-434.
13. O'Brien R J & Wong P C (2011) Amyloid precursor protein processing and Alzheimer's disease. *Annual review of neuroscience* 34:185-204.
14. Grundke-Iqbal I, et al. (1986) Abnormal phosphorylation of the microtubule-associated protein tau (tau) in Alzheimer cytoskeletal pathology. *Proceedings of the National Academy of Sciences* 83(13):4913-4917.
15. Holtzman D M, Mandelkow E, & Selkoe D J (2012) Alzheimer disease in 2020. *Cold Spring Harbor perspectives in medicine* 2(11):a011585.
16. Mudher A & Lovestone S (2002) Alzheimer's disease—do tauists and baptists finally shake hands? *Trends in neurosciences* 25(1):22-26.
17. Lansdall C J (2014) An effective treatment for Alzheimer's disease must consider both amyloid and tau. *Bioscience horizons* 7:1-11.
18. Smith M A, et al. (1995) Tau protein directly interacts with the amyloid β-protein precursor: implications for Alzheimer's disease. *Nature medicine* 1(4):365.
19. Giaccone G, et al. (1996) beta PP and Tau interaction. A possible link between amyloid and neurofibrillary tangles in Alzheimer's disease. *The American journal of pathology* 148(1):79.
20. Pundir S, Martin M J, O'Donovan C, & Consortium U (2016) UniProt tools. *Current protocols in bioinformatics* 53(1):1.29.21-21.29.15.
21. Altschul S F, Gish W, Miller W, Myers E W, & Lipman D J (1990) Basic local alignment search tool. *Journal of molecular biology* 215(3):403-410.
22. Wang Y & Ha Y (2004) The X-ray structure of an antiparallel dimer of the human amyloid precursor protein E2 domain. *Molecular cell* 15(3):343-353.
23. Neddens J, et al. (2018) Phosphorylation of different tau sites during progression of Alzheimer's disease. *Acta neuropathologica communications* 6(1):52.
24. Esparza T J, et al. (2016) Soluble amyloid-beta aggregates from human Alzheimer's disease brains. *Scientific reports* 6:38187.
25. Ganeshpurkar A, et al. (2019) Protein-Protein Interactions and Aggregation Inhibitors in Alzheimer's Disease. *Current topics in medicinal chemistry* 19(7):501-533.
26. Kupfer L, Hinrichs W, & Groschup M H (2009) Prion protein misfolding. *Current molecular medicine* 9(7):826-835.
27. Rossjohn J, et al. (1999) Crystal structure of the N-terminal, growth factor-like domain of Alzheimer amyloid precursor protein. *Nature Structural & Molecular Biology* 6(4):327.
28. Lee G, Cowan N, & Kirschner M (1988) The primary structure and heterogeneity of tau protein from mouse brain. *Science* 239(4837):285-288.
29. Sayas C L, et al. (2019) Role of tau N-terminal motif in the secretion of human tau by end binding proteins. *PloS One* 14(1):e0210864.
30. Oakley H, et al. (2006) Intraneuronal β-amyloid aggregates, neurodegeneration, and neuron loss in transgenic mice with five familial Alzheimer's disease mutations: potential factors in amyloid plaque formation. *Journal of Neuroscience* 26(40):10129-10140.
31. Rosenmann H, et al. (2008) A novel transgenic mouse expressing double mutant tau driven by its natural promoter exhibits tauopathy characteristics. *Experimental neurology* 212(1):71-84.
32. Westerman M A, et al. (2002) The relationship between Aβ and memory in the Tg2576 mouse model of Alzheimer's disease. *Journal of Neuroscience* 22(5):1858-1867.
33. Kanno T, Tsuchiya A, & Nishizaki T (2014) Hyperphosphorylation of Tau at Ser396 occurs in the much earlier stage than appearance of learning and memory disorders in 5×FAD mice. *Behavioural brain research* 274:302-306.

34. Vergara Panos C, et al. (2016) PHF-tau propagation in the presence of Amyloid ß pathology. in *6TH BELGIAN BRAIN CONGRESS* (Mons, Belgium), pp 8-10.
35. Polanco J G, et al. (2017) Amyloid-β and tau complexity—towards improved biomarkers and targeted therapies. *Nature Reviews Neurology* 14(1):22.
36. Trudler D, Weinreb O, Mandel S A, Youdim M B H, & Frenkel D (2014) DJ-1 deficiency triggers microglia sensitivity to dopamine toward a pro-inflammatory phenotype that is attenuated by rasagiline. *Journal of neurochemistry* 129(3):434-447.
37. Small S A & Duff K (2008) Linking Aβ and tau in late-onset Alzheimer's disease: a dual pathway hypothesis. *Neuron* 60(4):534-542.
38. Dou F, et al. (2003) Chaperones increase association of tau protein with microtubules. *Proceedings of the National Academy of Sciences* 100(2):721-726.
39. Leitner A, Walzthoeni T, & Aebersold R (2014) Lysine-specific chemical cross-linking of protein complexes and identification of cross-linking sites using LC-MS/MS and the xQuest/xProphet software pipeline. *Nature protocols* 9(1):120.
40. Leitner A, et al. (2014) Chemical cross-linking/mass spectrometry targeting acidic residues in proteins and protein complexes. *Proceedings of the National Academy of Sciences* 111(26):9455-9460.
41. Holmes K L & Lantz L M (2001) Protein labeling with fluorescent probes. *Methods Cell Biol* 63:185-203.
42. DeMattos R B, Bales K R, Cummins D J, Paul S M, & Holtzman D M (2002) Brain to plasma amyloid-β efflux: a measure of brain amyloid burden in a mouse model of Alzheimer's disease. *Science* 295(5563):2264-2267.
43. Webster S J, Bachstetter A D, Nelson P T, Schmitt F A, & Van Eldik L J (2014) Using mice to model Alzheimer's dementia: an overview of the clinical disease and the preclinical behavioral changes in 10 mouse models. *Frontiers in genetics* 5:88.
44. Heredia L, Torrente M, Colomina M T, & Domingo J L (2014) Assessing anxiety in C57BL/6J mice: a pharmacological characterization of the open-field and light/dark tests. *Journal of pharmacological and toxicological methods* 69(2):108-114.
45. Lifshitz V, et al. (2012) Immunotherapy of cerebrovascular amyloidosis in a transgenic mouse model. *Neurobiology of aging* 33(2):432. e431-432. e413.
46. Ji X, et al. (2017) Astaxanthin improves cognitive performance in mice following mild traumatic brain injury. *Brain research* 1659:88-95.

What is claimed is:

1. A method of alleviating symptoms of Alzheimer's Disease (AD) in a subject in need thereof comprising administering to the subject a therapeutically effective amount of at least one peptide comprising both the amino acid sequence as set forth in SEQ ID NO: 1 and the amino acid sequence as set forth in SEQ ID NO: 3, which prevents the binding of amyloid precursor protein (APP) to Tau protein, thereby treating the AD.

2. The method of claim 1, wherein said AD is associated with a mutation in said APP or said Tau protein.

3. The method of claim 1, wherein said binding is a covalent binding.

4. The method of claim 1, wherein said binding is between lysine 370 of said APP and lysine 387 on said Tau protein.

5. The method of claim 1, wherein said amino acid sequence as set forth in SEQ ID NO: 1 is connected to said amino acid sequence as set forth in SEQ ID NO: 3 by a linker.

6. The method of claim 5, wherein said at least one peptide comprises the sequence as set forth in SEQ ID NO: 5 or SEQ ID NO: 6.

7. The method of claim 1, wherein the total length of said at least one peptide is no longer than 70 amino acids.

8. The method of claim 1, wherein said administering comprises intranasally administering.

* * * * *

SEQUENCE LISTING

```
<160> NUMBER OF SEQ ID NOS: 15

<210> SEQ ID NO 1
<211> LENGTH: 23
<212> TYPE: PRT
<213> ORGANISM: Artificial sequence
<220> FEATURE:
<223> OTHER INFORMATION: synthetic peptides

<400> SEQUENCE: 1

His Phe Gln Lys Ala Lys Glu Arg Leu Glu Ala Lys His Arg Glu Arg
1               5                   10                  15

Met Ser Gln Val Met Arg Glu
            20


<210> SEQ ID NO 2
<211> LENGTH: 18
<212> TYPE: PRT
<213> ORGANISM: Artificial sequence
<220> FEATURE:
<223> OTHER INFORMATION: synthetic peptides

<400> SEQUENCE: 2

Ala Thr Val Ile Val Ile Thr Leu Val Met Leu Lys Lys Lys Gln Tyr
1               5                   10                  15

Thr Ser


<210> SEQ ID NO 3
<211> LENGTH: 16
<212> TYPE: PRT
<213> ORGANISM: Artificial sequence
<220> FEATURE:
<223> OTHER INFORMATION: synthetic peptides

<400> SEQUENCE: 3

Gly Leu Gly Asp Arg Lys Asp Gln Gly Gly Tyr Thr Met His Gln Asp
1               5                   10                  15
```

<210> SEQ ID NO 4
<211> LENGTH: 17
<212> TYPE: PRT
<213> ORGANISM: Artificial sequence
<220> FEATURE:
<223> OTHER INFORMATION: synthetic peptides

<400> SEQUENCE: 4

```
Lys Pro Gly Gly Gly Gln Val Glu Val Lys Ser Glu Lys Leu Asp Phe
1               5                   10                  15

Lys
```

<210> SEQ ID NO 5
<211> LENGTH: 54
<212> TYPE: PRT
<213> ORGANISM: Artificial sequence
<220> FEATURE:
<223> OTHER INFORMATION: synthetic peptides

<400> SEQUENCE: 5

```
His Phe Gln Lys Ala Lys Glu Arg Leu Glu Ala Lys His Arg Glu Arg
1               5                   10                  15

Met Ser Gln Val Met Arg Glu Gly Gly Gly Gly Ser Gly Gly Gly Gly
            20                  25                  30

Ser Gly Gly Gly Gly Ser Gly Leu Gly Asp Arg Lys Asp Gln Gly Gly
        35                  40                  45

Tyr Thr Met His Gln Asp
    50
```

<210> SEQ ID NO 6
<211> LENGTH: 54
<212> TYPE: PRT
<213> ORGANISM: Artificial sequence
<220> FEATURE:
<223> OTHER INFORMATION: synthetic peptides

<400> SEQUENCE: 6

```
His Phe Gln Lys Ala Lys Glu Arg Leu Glu Ala Lys His Arg Glu Arg
1               5                   10                  15

Met Ser Gln Val Met Arg Glu Glu Ala Ala Ala Lys Glu Ala Ala Ala
            20                  25                  30

Lys Glu Ala Ala Ala Lys Gly Leu Gly Asp Arg Lys Asp Gln Gly Gly
        35                  40                  45

Tyr Thr Met His Gln Asp
    50
```

<210> SEQ ID NO 7
<211> LENGTH: 770
<212> TYPE: PRT
<213> ORGANISM: Homo sapiens

<400> SEQUENCE: 7

```
Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60
```

```
Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
```

```
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
    610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
    690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770


<210> SEQ ID NO 8
<211> LENGTH: 441
<212> TYPE: PRT
<213> ORGANISM: Homo sapiens

<400> SEQUENCE: 8

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80
```

```
Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440
```

<210> SEQ ID NO 9
<211> LENGTH: 7
<212> TYPE: PRT
<213> ORGANISM: Artificial sequence
<220> FEATURE:
<223> OTHER INFORMATION: cell penetrating peptide (CPP) amino acid sequence

<400> SEQUENCE: 9

```
Tyr Gly Arg Lys Lys Arg Arg
1               5


<210> SEQ ID NO 10
<211> LENGTH: 11
<212> TYPE: PRT
<213> ORGANISM: Artificial sequence
<220> FEATURE:
<223> OTHER INFORMATION: cell penetrating peptide (CPP) amino acid
      sequence

<400> SEQUENCE: 10

Tyr Gly Arg Lys Lys Arg Arg Gln Arg Arg Arg
1               5                   10


<210> SEQ ID NO 11
<211> LENGTH: 5
<212> TYPE: PRT
<213> ORGANISM: Artificial sequence
<220> FEATURE:
<223> OTHER INFORMATION: cell penetrating peptide (CPP) amino acid
      sequence

<400> SEQUENCE: 11

Arg Arg Gln Arg Arg
1               5


<210> SEQ ID NO 12
<211> LENGTH: 15
<212> TYPE: PRT
<213> ORGANISM: Artificial Sequence
<220> FEATURE:
<223> OTHER INFORMATION: flexible peptide linker

<400> SEQUENCE: 12

Gly Gly Gly Gly Ser Gly Gly Gly Gly Ser Gly Gly Gly Gly Ser
1               5                   10                  15


<210> SEQ ID NO 13
<211> LENGTH: 54
<212> TYPE: PRT
<213> ORGANISM: Artificial Sequence
<220> FEATURE:
<223> OTHER INFORMATION: example of a peptide which comprises an APP
      derived peptide linked by a flexible peptide linker to a TAU
      derived peptide

<400> SEQUENCE: 13

His Phe Gln Lys Ala Lys Glu Arg Leu Glu Ala Lys His Arg Glu Arg
1               5                   10                  15

Met Ser Gln Val Met Arg Glu Gly Gly Gly Gly Ser Gly Gly Gly Gly
            20                  25                  30

Ser Gly Gly Gly Gly Ser Gly Leu Gly Asp Arg Lys Asp Gln Gly Gly
        35                  40                  45

Tyr Thr Met His Gln Asp
    50


<210> SEQ ID NO 14
<211> LENGTH: 15
<212> TYPE: PRT
<213> ORGANISM: Artificial Sequence
<220> FEATURE:
<223> OTHER INFORMATION: example of a rigid peptide linker

<400> SEQUENCE: 14
```

-continued

```
Glu Ala Ala Ala Lys Glu Ala Ala Ala Lys Glu Ala Ala Ala Lys
1               5                   10                  15


<210> SEQ ID NO 15
<211> LENGTH: 54
<212> TYPE: PRT
<213> ORGANISM: Artificial Sequence
<220> FEATURE:
<223> OTHER INFORMATION: example of a peptide which comprises an APP
      derived peptide linked by a rigid peptide linker to a TAU derived
      peptide

<400> SEQUENCE: 15

His Phe Gln Lys Ala Lys Glu Arg Leu Glu Ala Lys His Arg Glu Arg
1               5                   10                  15

Met Ser Gln Val Met Arg Glu Glu Ala Ala Ala Lys Glu Ala Ala Ala
            20                  25                  30

Lys Glu Ala Ala Ala Lys Gly Leu Gly Asp Arg Lys Asp Gln Gly Gly
        35                  40                  45

Tyr Thr Met His Gln Asp
    50
```